US008454511B2

(12) United States Patent
Milner et al.

(10) Patent No.: US 8,454,511 B2
(45) Date of Patent: *Jun. 4, 2013

(54) MAGNETO-MOTIVE ULTRASOUND DETECTION OF MAGNETIC NANOPARTICLES

(75) Inventors: Thomas E. Milner, Austin, TX (US); Marc D. Feldman, San Antonio, TX (US); Christopher Condit, Austin, TX (US); Jung-Hwan Oh, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 420 days.

This patent is subject to a terminal disclaimer.

(21) Appl. No.: 12/172,592

(22) Filed: Jul. 14, 2008

(65) Prior Publication Data
US 2009/0043198 A1 Feb. 12, 2009

Related U.S. Application Data

(63) Continuation-in-part of application No. 11/784,477, filed on Apr. 6, 2007, now Pat. No. 7,801,590, and a continuation-in-part of application No. 11/441,824, filed on May 26, 2006, now Pat. No. 7,983,737, and a continuation-in-part of application No. 11/620,562, filed on Jan. 5, 2007, now Pat. No. 8,162,834, and a continuation-in-part of application No. 11/550,771, filed on Oct. 18, 2006, now Pat. No. 8,036,732.

(60) Provisional application No. 60/949,460, filed on Jul. 12, 2007, provisional application No. 60/685,559, filed on May 27, 2005.

(51) Int. Cl.
*A61B 8/00* (2006.01)

(52) U.S. Cl.
USPC ........... 600/437; 600/407; 600/410; 600/443; 600/447

(58) Field of Classification Search
USPC ......... 600/1–4, 9–14, 437–458, 469; 424/9.5, 424/9.4–9.411
See application file for complete search history.

(56) References Cited

U.S. PATENT DOCUMENTS

| 4,676,980 A | 6/1987 | Segal et al. ..................... 424/85 |
| 4,816,567 A | 3/1989 | Cabilly et al. ................ 530/387 |
| 5,262,176 A | 11/1993 | Palmacci et al. ........... 424/9.322 |
| 5,565,332 A | 10/1996 | Hoogenboom et al. ...... 435/69.1 |
| 5,596,079 A | 1/1997 | Smith et al. .................. 530/328 |
| 5,824,520 A | 10/1998 | Mulligan-Kehoe ........ 435/91.41 |

(Continued)

FOREIGN PATENT DOCUMENTS

| WO | WO 93/06213 | 4/1993 |
| WO | WO 93/08829 | 5/1993 |

(Continued)

OTHER PUBLICATIONS

International Search Report, pp. 1-4 (Jun. 17, 2009).

(Continued)

*Primary Examiner* — Tse Chen
*Assistant Examiner* — Mark Remaly
(74) *Attorney, Agent, or Firm* — J. Peter Paredes; Rosenbaum IP

(57) ABSTRACT

Provided herein are systems, methods and compositions for the use of ultrasound for detection of cells and nanoparticles.

17 Claims, 7 Drawing Sheets

U.S. PATENT DOCUMENTS

| | | | |
|---|---|---|---|
| 5,991,697 A | 11/1999 | Nelson et al. | 702/49 |
| 6,031,071 A | 2/2000 | Mandeville et al. | 530/300 |
| 6,520,911 B1* | 2/2003 | Wen | 600/437 |
| 6,817,982 B2* | 11/2004 | Fritz et al. | 600/443 |
| 7,116,244 B2* | 10/2006 | Fling et al. | 340/870.26 |
| 2002/0193785 A1 | 12/2002 | Naghavi et al. | 606/28 |
| 2002/0198457 A1 | 12/2002 | Tearney et al. | 600/476 |
| 2003/0023153 A1 | 1/2003 | Izatt et al. | 600/407 |
| 2003/0055307 A1 | 3/2003 | Elmaleh et al. | 600/1 |
| 2004/0023415 A1 | 2/2004 | Sokolov et al. | 436/518 |
| 2004/0064050 A1* | 4/2004 | Liu et al. | 600/457 |
| 2004/0254419 A1 | 12/2004 | Wang et al. | 424/422 |
| 2005/0165298 A1 | 7/2005 | Larson et al. | 600/410 |
| 2005/0171433 A1* | 8/2005 | Boppart et al. | 600/473 |
| 2005/0256207 A1 | 11/2005 | McGrath | 514/674 |
| 2006/0140871 A1 | 6/2006 | Sillerud | 424/9.36 |
| 2006/0232272 A1* | 10/2006 | Hanley | 324/309 |
| 2007/0010702 A1 | 1/2007 | Wang et al. | 600/8 |
| 2007/0038121 A1 | 2/2007 | Feldman et al. | 600/476 |
| 2007/0161893 A1 | 7/2007 | Milner et al. | 600/425 |
| 2007/0260138 A1 | 11/2007 | Feldman et al. | 600/409 |
| 2008/0097185 A1 | 4/2008 | Feldman et al. | 600/407 |
| 2008/0097194 A1 | 4/2008 | Milner | 600/425 |

FOREIGN PATENT DOCUMENTS

| | | |
|---|---|---|
| WO | WO 96/23524 | 8/1996 |
| WO | WO 99/13916 | 3/1999 |
| WO | WO 2004/096049 | 11/2004 |
| WO | WO 2006/020903 | 2/2006 |

OTHER PUBLICATIONS

Written Opinion of the International Searching Authority, pp. 1-3 (Jun. 17, 2009).

Aaron et al. Increased optical contrast in imaging of epidermal growth factor receptor using magnetically actuated hybrid gold/iron oxide nanoparticles. Optics Express (2006) 14(26):12930-12943.

Alder et al. Phase-sensitive optical coherence tomography at up to 370,000 line per second using buffered Fourier domain mode-locked lasers. Optics Letters (2007) 32:626-628.

Alivisatos. The use of nanocrystals in biological detection. Nature Biotechnology (2006) 22(1):47-52.

Anderson et al. Selective photothermolysis: precise microsurgery by selective absorption of pulsed radiation. Science (1983) 220:524-527.

Asian et al. Tunable plasmonic glucose sensing based on the dissociation of Con A aggregated dextran-coated gold colloids. Analytica Chimica Acta (2004) 517:139-144.

Brezinski et al. Optical coherence tomography for optical biopsy. Circulation (1996) 93:1206-1213.

Caplan et al. Near-infrared spectroscopy for the detection of vulnerable coronary artery plaques. Journal of the American College of Cardiology (2006) 47:C92-C96.

Chen et al. Optical Doppler tomographic imaging of fluid flow velocity in highly scattering media. Optics Letters (1997) 22(1):64-66.

Cilingiroglu et al. Detection of vulnerable plaque in a murine model of atherosclerosis with optical coherence tomography. Catheterization and Cardiovascular Interventions (2006) 67:915-923.

Clackson et al. Making antibody fragments using phage display libraries. Nature (1991) 352:624-628.

Daniel et al. Gold nanoparticles: assembly, supramolecular chemistry and application toward biology, catalysis and nanotechnology. Chemical Reviews (2004) 104:293-346.

Dave et al. Abstract: Polarization-maintaining fiber-based optical low-coherence reflectometer for characterization and ranging of birefringence. Optics Letters (2003) 28(19):1775-1777.

Dave et al. Optical low-coherence reflectometer for differential phase measurement. Optical Letters (2000) 25:227-229.

David et al. Protein Iodination with Solid State Lactoperoxidase. Biochemistry (1974) 13(5):1014-1021.

DeBoer et al. "Polarization-sensitive optical coherence tomography." Handbook of Optical Coherence Tomography. New York: Marcel Dekker Inc., 2002. 237-274.

Elghanian et al. Selective colorimetric detection of polynucleotides based on the distance-dependent optical properties of gold nanoparticles. Science (1997) 277:1078-1081.

Fujimoto et al. High resolution in vivo intra-aterial imaging with optical coherence tomography. Heart (1999) 82:128-133.

Griffiths et al. Isolation of high affinity human antibodies directly from large synthetic repertoires. The EMBO Journal (1994) 13(14):3245-3260.

Griffiths et al. Human anti-self antibodies with high specificity from phage display libraries. The EMBO Journal (1993) 12(2):725-735.

Huber et al. Buffered Fourier domain mode locking: Unidirectional swept laser sources for optical coherence tomography imaging at 370,000 lines/s. Optics Letters (2006) 31:2975-2977.

Huber et al. Fourier domain mode locking (FDML): A new laser operating regime and applications for optical coherence tomography. Optics Express (2006) 14:3225-3237.

Hunter et al. Preparation of Iodine-131 Labelled human growth hormone of high specific activity. Nature (1962) 194(4827):495-496.

Jakobovits et al. Analysis of homozygous mutant chimeric mice: Deletion of the immunoglobulin heavy-chain joining region blocks B-cell development and antibody production. PNAS (1993) 90:2551-2555.

Jakobovits et al. Germ-line transmission and expression of a human-derived yeast artifical chromosome. Nature (1993) 362:255-258.

Jang et al. Visualization of coronary atherosclerotic plaques in patients using optical coherence tomography: Comparison with intravascular ultrasound. Journal of the American College of Cardiology (2002) 39:604-609.

Johnson et al. Plaque rupture after short periods of fat feeding in the apolipoprotein E knockout mouse: model characterization and effect of Pravastatin treatment. Circulation (2005) 111:1422-1430.

Johnson et al. Human antibody engineering. Current Opinion in Structural Biology (1993) 3:564-571.

Jones et al. Replacing the complementarity-determining regions in a human antibody with those from a mouse. Nature (1986) 321:522-525.

Josephson et al. High-efficiency intracellular magnetic labeling with novel superparamagnetic-tat peptide conjugates. Bioconjugate Chemistry (1999) 10:186-191.

Kane. Introduction to Physics in Modern Medicine. London: Taylor and Francis Publishers, 2003. http://books.google.com/books?id=NtNjV9Lx-T8C.

Kelly et al. Detection of Vascular Adhesion Molecule-1 expression using a novel multimodal nanoparticle. Circulation Research (2005) 96:327-336.

Kemp et al. High-sensitivity determination of birefringence in turbid media with enhanced polarization-sensitive optical coherence tomography. Journal of the Optical Society of America (2005) 22(3):552-560.

Kim et al. Hemoglobin contrast in magnetomotive optical Doppler tomography. Optics Letters (2006) 31(6):778-780.

Kohler et al. Continuous cultures of fused cells secreting antibody of predefined specificity. Nature (1975) 256:495-497.

Kozbor et al. A human hybrid myeloma for production of human monoclonal antibodies. The Journal of Immunology. (1984) 133(6):3001-3005.

Kuo et al. Polarization-sensitive optical coherence tomography for imaging human atherosclerosis. Applied Optics (2007) 46:2520-2527.

Landini et al. New technological developments in the clinical imaging of atherosclerotic plaque. Current Pharmaceutical Design (2003) 9:2403-2415.

Lee et al. Engineered microsphere contrast agents for optical coherence tomography. Optics Letters (2003) 28(17):1546-1548.

Leitgeb et al. Performance of Fourier domain vs time domain optical coherence tomography. Optics Express (2003) 11:889-894.

Loo et al. Nanoshell-enabled photonics-based imaging and therapy of cancer. Technology in Cancer Research and Treatment. (2004) 3(1):33-40.

MacNeill et al. Intravascular modalities for detection of vulnerable plaque. Arteriosclerosis, Thrombosis, and Vascular Biology (2003) 23:1333-1342.

Mandel et al. Magnetite nanoparticles with tunable gold or silver shell. Journal of colloid and interface science (2005) 286:187-194.

Marks et al. By-passing immunization: building high affinity human antibodies by chain shuffling. Nature Biotechnology (1992) 10:779-783.

Marks et al. By-passing Immunization Human Antibodies from V-gene Libraries Displayed on Phage. Journal of Molecular Biology (1991) 222:581-597.

McCafferty et al. Phage antibodies: filamentous phage displaying antibody variable domains. Nature (1990) 348:552-554.

Milstein et al. Hybrid hybridomas and their use in immunohistochemistry. Nature (1983) 305:537-540.

Mindlin. Force at a point in the interior of a semi-infinite solid. Physics (1936) 7:195-202.

Moreno et al. Detection of high risk atherosclerotic coronary plaques by intravascular spectroscopy. Journal of Interventional Cardiology (2003) 16:243-252.

Mornet et al. Magnetic nanoparticle design for medical diagnosis and therapy. Journal of Materials Chemistry (2004) 14:2161-2175.

Morrison et al. Chimeric human antibody molecules: Mouse antigen-binding domains with human constant region domains. PNAS (1984) 81:6851-6855.

Motta et al. High magnetic field effects on human deoxygenated hemoglobin light adsorption. Bioelectrochemistry and Bioenergetics (1998) 47:297-300.

Munson et al. Ligand: A Versatile Computerized Approach for Characterization of Ligand-Binding Systems. Analytical Biochemistry. (1980) 107:220-239.

Nakamura et al. Identification and treatment of vulnerable plaque. Reviews in Cardiovascular Medicine (2004) 5(Suppl. 2):S22-S33.

Nogueira et al. Raman spectroscopy study of atherosclerosis in human carotid artery. Journal of Biomedical Optics (2005) 10(3):031117.

Nygren. Conjugation of horseradish peroxidase to Fab fragments with different homobifunctional and heterobifunctional cross-linking reagents. The journal of histochemistry and cytochemistry (1982) 30(5):407-412.

Oh et al. Magneto-motive detection of tissue-based macrophages by differential phase optical coherence tomography. Lasers in Surgery and Medicine (2007) 39(3):266-272.

Oh et al. Detection of magnetic nanoparticles in tissue using magneto-motive ultrasound. Nanotechnology (2006) 17:4183-4190.

Oldenburg et al. Imaging magnetically labeled cells with magnetomotive optical coherence tomography. Optics Letters (2005) 30:747-749.

Oldenburg et al. Magnetic contrast agents for optical coherence tomography. Proceedings of SPIE (2004) 5316:26-28.

Oldenburg et al. Infrared extinction properties of gold nanoshells. Applied Physics Letters (1999) 75:2897-2899.

Oldenburg et al. Nanoengineering of optical resonances. Chemical Physics Letters (1998) 288:243-247.

Pain et al. Preparation of protein a-peroxidase monoconjugate using a heterobifunctional reagent and its use in enzyme immunoassays. Journal of Immunological Methods (1981) 40:219-230.

Piao et al. Quantifying Doppler angle and mapping flow velocity by a combination of Doppler-shift and Doppler-bandwidth measurements in optical Doppler tomography. Applied Optics (2003) 42(25):5158-5166.

Pitsillides et al. Selective cell targeting with light-absorbing microparticles and nanoparticles. Biophysical Journal (2003) 84:4023-4032.

Raghunand et al. Microenvironmental and cellular consequences of altered blood flow in tumours. The British Journal of Radiology (2003) 76:S11-S22.

Regar et al. Optical coherence tomography. Cardiovascular Radiation Medicine (2003) 4(4): 198-204.

Reynolds et al. Method of determining nanoparticle core weight. Analytical Chemistry (2005) 77:814-817.

Riechmann et al. Reshaping human antibodies for therapy. Nature (1988) 332:323-327.

Robles et al. Short-Duration High-Frequency Quasi-Sinusoidal Magnetic Field Generator. IEEE transactions on instrumentation and measurement (2005) 54(6): 2481-2485.

Rylander et al. Quantitative phase-contrast imaging of cells with phase-sensitive optical coherence microscopy. Optics Letters (2004) 29(13):1509-1511.

Schenck. Physical interactions of static magnetic fields with living tissues. Progress in Biophysics and Molecular Biology (2005) 60:1177-1181.

Shen et al. Manocrystalline iron oxide nanocompounds (MION): Physicochemical properties. Magnetic Resonance Medicine (1993) 29:599-604.

Siiman et al. Surface-enhanced Raman scattering (SERS) of random silver or gold particle arrays on aminodextran-coated polystyrene beads. Journal of Raman Spectroscopy (2005) 36:1125-1133.

Siiman et al. Fluorescent neoglycoproteins : Antibody-aminodextran-phycobiliprotein conjugates. Bioconjugate Chemistry (1999) 10:1090-1106.

Silveira et al. Correlcation between near-infrared Raman spectroscopy and the histopathological analysis of atherosclerosis in human coronary arteries. Lasers in Surgery and Medicine (2002) 30(4):290-297.

Sirol et al. Molecular imaging for the diagnosis of high-risk plaque. Cardiovascular Research (2003) 96(12):1219-1224.

Sun et al. Development of nanoparticle libraries for biosensing. Bioconjugate Chemistry (2006) 17:109-113.

Sun et al. Increased sensitivity of surface Plasmon resonance of gold nanoshells compared to that of fold solid colloids in response to environmental changes. Analytical Chemistry (2002) 74:5297-5305.

Suresh et al. Bispecific Monoclonal Antibodies from Hybrid Hybridomas. Methods in Enzymology (1986) 121:210-228.

Taylor et al. The magnetic susceptibility of the iron in ferrohemoglobin. Journal of the American Chemical Society (1938) 60:1177-1181.

Tearney et al. Quantification of macrophage content in atherosclerotic plaques by optical coherence tomography. Circulation (2003) 107:113-119.

Traunecker et al. Bispecific single chain molecules (Janusins) target cytotoxic lymphocytes on HIV infected cells. The EMBO Journal. (1991) 10(12):3655-3659.

Vakoc et al. Phase-resolved optical frequency domain imaging. Optics Express (2005) 13:5483-5493.

Verhoeyen et al. Reshaping Human Antibodies: Grafting an anti-lysozyme activity. Science (1988) 239:1534-1536.

Villard et al. Use of blood substitute to determine instantaneous murine right ventricular thickening with optical coherence tomography. Circulation (2002) 105:1843-1849.

Wang L et al. Monodispersed core-shell $Fe_3O_4$@Au nanoparticles. The Journal of Physical Chemistry B (2005) 109:21593-21601.

Wang T et al. Immobilization and characterization of g-Aminobutyric acid on gold surface. Journal of Biomedical Materials Research, Part A (2006) 79A:201-209.

Wang X et al. Abstract: Characterization of fluid flow velocity of optical Doppler tomography. Optics Letters (1995) 20(11):1337-1339. http://www.opticsinfobase.org/abstract.cfm?&uri=ol-20-11-1337.

Waterhouse et al. Combinatorial infection and in vivo recombination: a strategy for making large phage antibody repertoires. Nucleic Acids Research (1993) 21(9):2265-2266.

Weissleder et al. Cell-specific targeting of nanoparticles by multivalent attachment of small molecules. Nature Biotechnology (2005) 23:1418-1423.

Weissleder. A clearer vision for in vivo imaging. Nature Biotechnology (2001) 19:316-317.

Yamamoto et al. A blood-oxygenation-dependent increase in blood viscosity due to a static magnetic field. Physics in Medicine and Biology (2004) 49:3267-3277.

* cited by examiner

FIGURE 8B
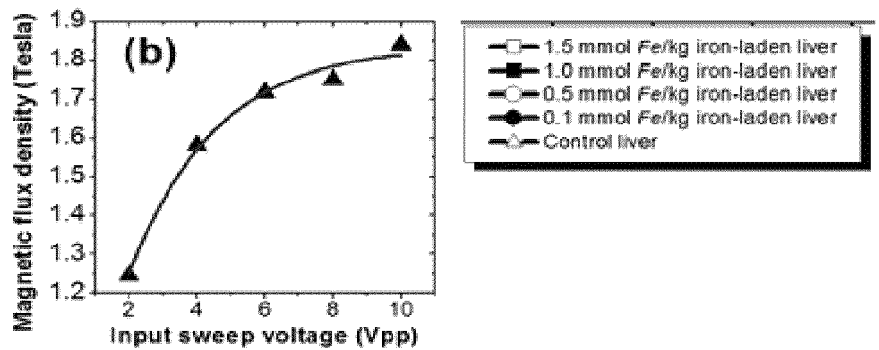
FIGURE 9A                                FIGURE 9B
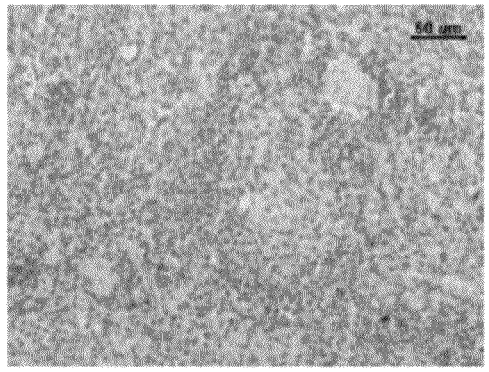    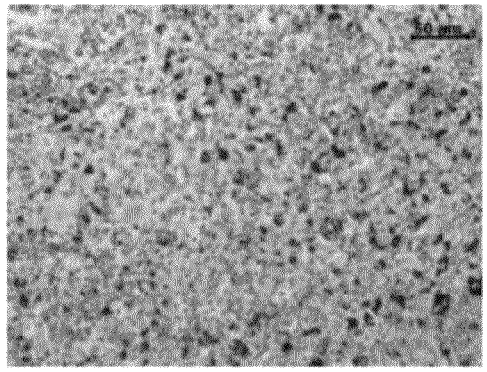
FIGURE 10
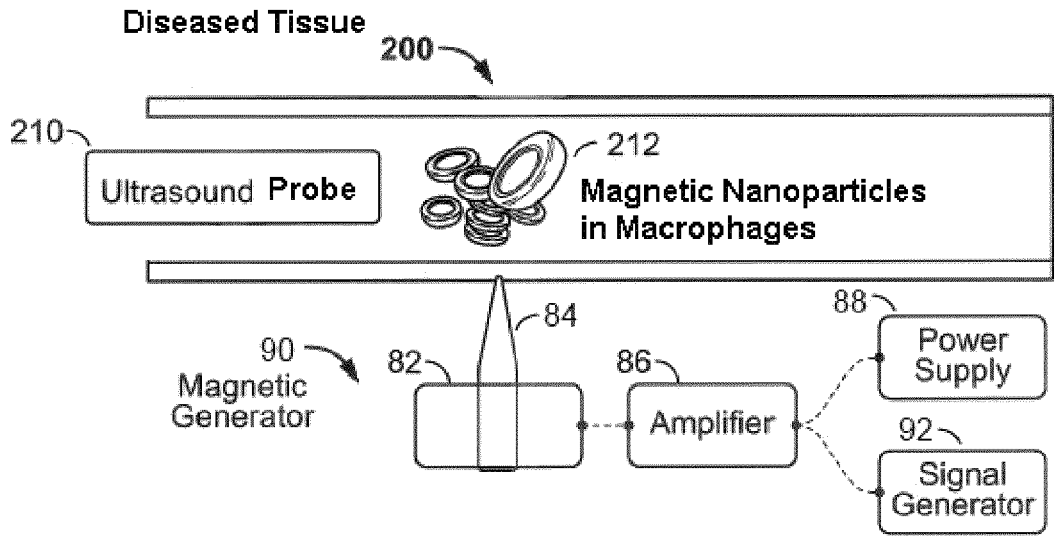

MAGNETO-MOTIVE ULTRASOUND DETECTION OF MAGNETIC NANOPARTICLES

CROSS-REFERENCE TO RELATED APPLICATIONS

This application claims priority to provisional application Ser. No. 60/949,460, filed Jul. 12, 2007, and this application is a continuation-in part of application Ser. No. 11/784,477, filed Apr. 6, 2007, now U.S. Pat. No. 7,801,590, which is a continuation-in-part of application Ser. No. 11/441,824, filed May 26, 2006, now U.S. Pat. No. 7,983,737, which claims the benefit of U.S. Provisional Application No. 60/685,559, filed on May 27, 2005; and the application is also a continuation-in-part of application Ser. No. 11/620,562, filed on Jan. 15, 2007, now U.S. Pat. No. 8,162,834, which is a continuation-in-part of application Ser. No. 11/550,771, filed on Oct. 18, 2006, now U.S. Pat. No. 8,036,732. The aforementioned applications are herein incorporated by reference in their entirety.

BACKGROUND

Ultrasound is a broadly used tool in medical imaging and it has several advantages over other imaging techniques such as MRI and computed tomography ("CT"). Ultrasound is a real-time, nonionizing, cost effective, portable, and widely available imaging modality. Ultrasound contrast agents have enabled researchers to expand their investigations into molecular scales, contributing to increased contrast enhancement and also contrast-specific imaging. The most common ultrasound contrast agents, composed of specific gaseous microbubbles in a core shell, have been investigated to enhance contrast in ultrasound medicine. Compared to the surrounding tissue, microbubbles present a large acoustic impedance mismatch in tissues and thus produce a strong backscattered sound signal. In addition, microbubbles are used in harmonic and subharmonic imaging to improve the subjective image quality. Although microbubbles play an important role in increasing the enhancement of the diagnostic potential of ultrasound imaging, the micron-sized bubbles have limited use in molecular imaging because these agents are too large to pass through the pulmonary and systemic capillary bed. Moreover, microbubbles are unstable, have a short blood half-life and a propensity to fracture and collapse when exposed to ultrasound waves. Furthermore, microbubbles need sufficient acoustic pressure to increase contrast. These features have limited the use of microbubbles in ultrasound molecular imaging. To overcome the size effects and increase the efficacy of enhancement imaging, perfluorocarbon emulsion nanoparticles ("PFC"), approximately 250 nm in diameter, were reported as an alternative ultrasound contrast agent. Nanometer-sized ultrasound contrast agents may penetrate the large capillary bed, but penetration to vascular targets and extravasations through tight capillary pores could be inhibited due to their relatively large size. Unfortunately, PFC ultrasound contrast agents produced a smaller acoustic impedance mismatch, a weaker ultrasound reflected signal, and create less contrast enhancement of echogenic images than gaseous microbubbles.

Superparamagnetic iron oxide ("SPIO") nanoparticles have been well established over the past decade as a contrast enhancement for MRI imaging. Early studies demonstrated that SPIO nanoparticles can improve the detection of liver metastases in patients. After SPIO nanoparticles have been administrated intravenously, tissue-based macrophages (Kupffer cells) in the body take up SPIO nanoparticles through the reticulo endothelial system ("RES") including bone marrow, hepatic lesions, lymph node metastases in cancer, and spleen. Compared to conventional ultrasound contrast agents, magnetically activated SPIO nanoparticles have several advantages, including small size, strong magnetic susceptibility, and bio-safety. These nanoparticles (µ20 nm core size) allow transport through the microvasculature and enable passage through the endothelium while retaining their super paramagnetic properties. Since SPIO nanoparticles for tissue-specific MRI contrast agents were approved by the FDA in 1996, to date, these magnetic nanoparticles have been used in various clinical applications without safety concerns associated with alternative contrast agents.

The present application improves ultrasound imaging.

SUMMARY OF THE INVENTION

Provided herein are systems, methods and compositions for the detection of cells using ultrasound using nanoparticles.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

FIG. 8B is a graph showing the magnetic flux density of the swept frequency input signal versus input peak-to-peak voltage.

FIGS. 9A-9B are histological cross-section of iron-laden liver with Prussian blue stain, where 9A is the control specimen and 9B is a specimen with a high concentration of iron (1.5 mmol Fe/kg body weight); and FIGS. 9A-9B are both observed (magnification: 20), where the blue color regions are iron oxide nanoparticles engulfed by liver-based macrophage Kupffer cells.

FIG. 10 is a schematic diagram of the Magneto-Motive Ultrasound probe for intravascular techniques.

DETAILED DESCRIPTION OF THE INVENTION

Provided herein are methods, compositions and apparatuses for detecting a cell and/or a metallic composition using ultrasound and optionally killing the cell. By a "cell" is meant one or more cell of, or derived from, a living organism or subject. The cell or cells can be located within a subject or can be located ex vivo. The disclosed methods, compositions and apparatuses for detecting a cell and/or a metallic composition are described herein variously by reference to cell(s), composition(s) and/or metallic composition(s). It will be understood that description of various aspects of the disclosed methods, compositions and apparatuses by reference to one or a subset of cell(s), composition(s) or metallic composition(s) constitutes description of that aspect of the disclosed methods, compositions and apparatuses to the non-referenced cell(s), composition(s) and metallic composition(s), unless the context clearly indicates otherwise.

In one embodiment, the method for detecting a cell comprises applying a magnetic field to the cell. A cell can comprise a cellular membrane and a metallic composition. Optionally, the metallic composition is a metallic nanoparticle that was administered to the subject or otherwise brought into contact with the cell. In another exemplary method for detecting a cell by ultrasound, light energy can cause a change in the cell. For example, a pulsed laser can be used to cause movement of the metallic composition comprised by the cell.

The metallic composition can be located within the cell, including in the cell's cellular membrane, or on the outside of the cell. If the metallic composition is a metallic nanoparticle located on the outside of the cell, it can be connected or targeted to the exterior surface of the cell's cellular membrane. Exemplary methods of targeting or connecting a metallic composition to a cell are described herein.

Figure 1:
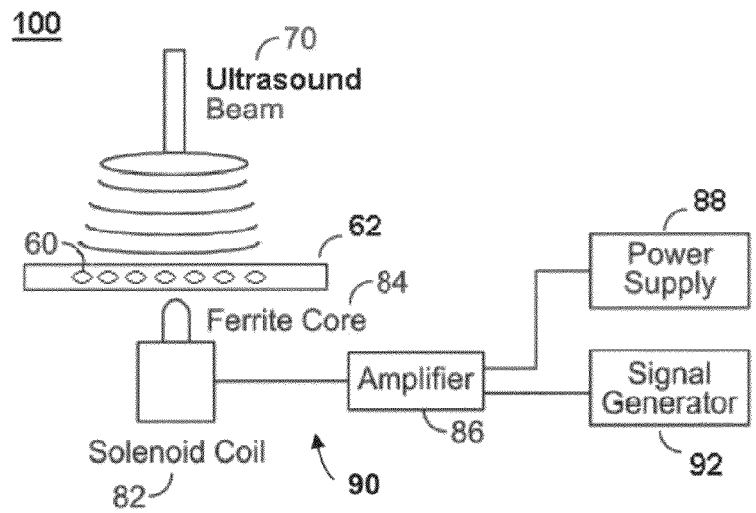
FIG. 1 is a schematic diagram of the setup with the magnetic field generator and conical iron core inside the solenoid.

Generally speaking, a system and method for detecting nanoparticles by Magneto-Motive Ultrasound ("MM-US") is described herein. By combining a high strength magnetic field to excite iron-laden tissue, ultrasound detects the detectable internal strain field or induced tissue motion, as disclosed by inventors in Nanotechnology 17: 4183-4190 (2006), herein incorporated by reference. As shown in FIG. 1, the MM-US system 100 comprises an ultrasound beam 70, metallic compositions 60, and a magnetic field generator 90. The magnetic field generator 90 includes a solenoid coil 82 (Ledex 4EF) with a conical iron-ferrite core 84 at the center driven by a current amplifier 86, a signal generator 92 (HP 33120A, Hewlett Packard Inc., USA), and a regulated DC power supply 88. The magnetic field generator 90 can be placed near a tissue or cell 62 containing nanoparticles 60 during MM-US imaging. The combination of the ferrite core 84 and solenoid coil 82 using a high power operation increases the magnetic field substantially and focuses the magnetic field strength ($B_{max}$=2 T). The magnetic force on the metallic composition 60 is varied by applying a sinusoidal current to the solenoid 82 containing a conical iron-ferrite core 84 to generate a detectable internal strain field on the cell 62. A detectable internal strain field may be any microscale displacement of the nanoparticle or nanoparticle-tissue conglomerates, which is detected by ultrasound.

Ultrasound imaging systems can be equipped with a 38 mm aperture, broadband (5-10 MHz) linear array transducer. Cells can be imaged in color power Doppler, power Doppler, M-mode and B-scan modes. B-scan sonogram images, also called the grayscale mode, are the typical ultrasound method to monitor or examine the human body using backscattering of acoustic waves. M-mode ultrasound employs a sequence of scans at a fixed ultrasound beam over a given time period. M-mode is used for visualizing rapidly moving subjects, such as heart valves. Compared to conventional B-scan images, Doppler ultrasound is used to assess changes in the frequency of reflected acoustic waves. Color power Doppler converts reflected acoustic waves that are Doppler shifted into colors that overlay the conventional B-scan images and can indicate the speed and direction of moving objects. Power Doppler ultrasound is most commonly used to evaluate moving objects and has higher sensitivity than the color power Doppler mode. The gain of the color power and Doppler imaging mode can be manually adjusted to suppress the background noise. If the settings of the ultrasound instrumentation remain unchanged, objective comparisons of each can be made.

Alternatively, the MM-US imaged nanoparticles can then be affected with an energy capable of heating the metallic composition, wherein the heating is sufficient to kill, lyse the cell, or lethally injure the detected cell. Other non-limiting examples of energy that can be applied to kill a cell include any energy that can move the nanoparticle of the cell. Movement of the particle can be used to heat the particle to a sufficient degree to kill or lyse the cell. For example, magnetic, light, or sonic energy can be used.

An effective cell killing protocol can vary with such factors as the particular cell being killed, the tissue in proximity to the cell, the type and composition and characteristics of the particle, the number of particles, the type of pathology being treated, the duration of the treatment, characteristics of the treatment (i.e. wavelength, fluence, pulse duration and number of pulses) the nature of concurrent therapy (if any), the type of energy being applied to contact the particle of the cell, the properties of the surrounding media or amount of water. An effective killing protocol can be readily determined by one of ordinary skill in the art using routine experimentation.

After detecting a cell by MM-US, for example a macrophage associated with vulnerable plaque, the system can further comprise an energy source for heating the metallic particle or composition. The source can provide energy for heating the composition that is sufficient to kill or lethally injure the detected cell. In some exemplary aspects, the system can further comprise an energy source for causing a non-lethal change in the cell. For example, the energy source for causing a non-lethal change in the cell can produce a magnetic field. The energy source for causing a non-lethal change in the cell can also produce light or sound. The energy source for causing the non-lethal change in the cell and the energy source for heating the metallic particle can be of the same type. For example, each energy source can generate and/or transmit sound energy. In some exemplary aspects, the energy source for causing the non-lethal change in the cell and the energy source for heating the metallic particle are the same source. In other exemplary aspects, the energy source for causing the non-lethal change in the cell and the energy source for heating the metallic particle are different sources and/or different types of energy. For example, the energy sources for causing the non-lethal change can generates and/or transmit magnetic filed energy and the energy source for causing the heating can generate and/or transmits light energy. Thus, in some exemplary aspects the systems described herein can comprise at least three separate sources of energy. One source of energy can be the magnetic energy used for MM-US imaging, as described previously. Such magnetic energy can be referred to as imaging magnetic energy. A second source can be used to produce energy to cause heating of the metallic composition comprised by the cell to kill or lethally injure the cell. Such sources can increase the temperature of a metallic particle in the cell. For example, any source that can increase the particle temperature can be used. Exemplary sources include light energy sources and magnetic force generators that can cause an increase in temperature of the particle by inducing movement of the particle. Such sources to cause lethal changes in a cell can comprise magnetic fields, light, sound and any other energy that can cause lethal changes to a cell. The magnetic fields may also be oscillating or alternating or a DC magnetic field.

The detectable internal strain field can be generated in a cell when a metallic composition, including a metallic nanoparticle, is under the action of an external force. The internal strain field can be detected using ultrasound imaging. The external force may be provided by the application of an external magnetic flux density (B). An external force on the nanoparticle may be induced by the interaction of the external magnetic flux density (B) with an induced magnetic moment in the nanoparticle (paramagnetic or diamagnetic) or with a permanent magnetic moment (ferromagnetic) in the nanoparticle. Action of the external force on each metallic composition can produce movement of the metallic composition ($z_{np}$(t)) that produces a change in the cellular membrane tension level or an internal strain field within a cell. Action of a force on each metallic composition in a cell or tissues produces a movement of the metallic composition ($z_{np}$(t)). Movement of the metallic composition can be along the z-direction. The metallic composition can also have movement in any direction that can be written as vector displacement, $u_{np}(r_o)$ for a metallic composition positioned at $r_o$. Metallic composition displacement $u_{np}(r_o)$ can produce a displacement field (u(r, $r_o$)) in the proteins in the cell containing the metallic composition and surrounding cells. In the case of a homogeneous elastic media, the displacement field (u(r, $r_o$)) can be computed by tissue biomechanical methods, which are well known in the art. The displacement field (u(r, $r_o$)) produced by a metallic composition positioned at $r_o$ can induce an internal strain field that is determined by change in the displacement field along a particular direction. The strain field ($\epsilon_{ij}$(r, $r_o$)) is a tensor quantity and is given by, $$\varepsilon(r, r_0) = \frac{\partial u(r, r_0)}{\partial x_j}$$

where $u_i$(r, $r_o$) is the i'th component of the displacement field and $x_j$ is the $j^{th}$ coordinate direction. For example, when j=3, $x_3$ is the z-direction. The internal strain field in a cell due to all metallic compositions in the cell and surrounding cells is a superposition of the strain fields due to each metallic composition. A detectable change in a cell can also be caused with light energy. For example, pulsed laser light can be applied to contact a metallic particle comprised by a cell including in a cell either naturally occurring or administered exogenously. The application of light energy can cause a detectable change due to a change in optical refractive and thermal elastic expansion. The light energy can also cause motion of the cell, particle, or tissues proximate to the cell for detection by ultrasound, light is absorbed by the nanoparticle and generates an acoustic wave that is detected by an acoustic transducer. Alternatively, sound energy can motion of the cell, particle, or tissues proximate to the cell for detection by ultrasound.

Metallic Nanoparticles

The metallic composition can comprise a plurality of metallic nanoparticles. The nanoparticles can be substantially spherical in shape and can have a diameter from about 0.1 nanometers (nm) to about 1000.0 nm. The nanoparticles are not, however, limited to being spherical in shape. Thus, the nanoparticles are asymmetrical in shape. If the nanoparticles are asymmetrical in shape, the largest cross sectional dimension of the nanoparticles can be from about 0.1 nanometers (nm) to about 1000.0 nm in length. The metallic composition can comprise metal having non-zero magnetic susceptibility or zero magnetic susceptibility or combinations of non-zero and zero magnetic susceptibility metals. In addition, the metallic composition may be ferromagnetic and thereby contain a permanent magnetic moment. Thus, if the composition comprises nanoparticles, the nanoparticles can all have a non-zero magnetic susceptibility or a zero magnetic susceptibility or a combination of particles having a non-zero magnetic susceptibility and a zero magnetic susceptibility. Metallic compositions having a non-zero magnetic susceptibility can comprise a material selected from the group consisting of iron oxide, iron, cobalt, nickel, chromium and combinations thereof. The metallic compositions can comprise metal having non-zero electrical conductivity or zero electrical conductivity or combinations of non-zero and zero electrical conductivity metals. Also provided is a method for detecting a composition, the method wherein the composition comprises a magnetic or paramagnetic material. Any magnetic or paramagnetic material, whether metallic or non-metallic, can be used in the described methods or with the described systems. In this regard, any material can be used that can cause a change in a cell or can be detected using ultrasound when contacted with an applied magnetic field. Similarly, nonmetallic, non-magnetic particles can be used to cause a change in a cell or can be detected using ultrasound when contacted with an applied magnetic field using the methods and systems described herein. Also, as described herein, a pulsed light source can be applied to a cell, typically in pulse duration from 5 fs-50 ns and light from a pulsed laser source is absorbed by the nanoparticle and generates an acoustic wave that is detected by an acoustic transducer.

The systems, apparatuses and methods can be practiced using metallic compositions without magnetic susceptibility. When using metallic compositions without magnetic susceptibility, or when using compounds having a non-zero magnetic susceptibility, an electrical eddy current can be induced in the composition by a changing magnetic flux density.

To induce an eddy current in a metallic composition a first time-varying magnetic field can be applied to a cell. The first magnetic field can interact with a metallic composition within or external to the cell to induce an electrical eddy current within the metallic composition. A second magnetic field can be applied to the cell that interacts with the induced eddy current to cause a change in the cell. The cell can be detected by detecting the change in the cell caused by the interaction of the second magnetic field with eddy current using an ultrasound modality. Exemplary changes in the cell caused by the interaction of the second magnetic field with the eddy current include movement of the cell, movement of the metallic composition, a change in the cellular membrane tension level, and a change in the internal strain field of the cell.

Thus, a metallic composition or a nanoparticle that does not have a significant magnetic permeability can be used. For example, although gold nanoparticles do not have significant magnetic permeability many target-specific molecular agents (e.g., antibodies) can be conjugated to the nanoparticle surface. When using a high-conductivity particle for detection, a magnetic dipole can be induced in the particle by exposing to a time-varying magnetic field (B(t)).

The time-varying magnetic field (B(t)) can cause an electromotive force or potential in the particle that can induce a volumetric and surface electric eddy-current in the high conductivity nanoparticle. Exemplary circuitry for a magnetic pulser that can be used to produce an eddy current is described in G H Schroder, Fast pulsed magnet systems, Handbook of Accelerator Physics and Engineering, A. Chao and M. Tinger, Eds. 1998 or in IEEE transactions on instrumentation and measurement, VOL. 54, NO. 6, December 2005, pp 2481-2485, which is incorporated herein by reference for the circuitry and methods described therein.

The eddy-current can produce time-varying magnetic moment that can interact with a second applied magnetic field (B). The induced eddy-current in the high-conductivity nanoparticle or metallic composition and the second applied magnetic field can interact to produce a torque or twist and or force on the nanoparticle or metallic composition. The induced torque can twist or move the nanoparticle that is mechanically linked to a target in the cell (e.g., the membrane) or located inside the cell. The displacement or twisting motion of the nanoparticle can modify the internal strain field of the cell (surrounding cells and tissue) which can be detected using phase sensitive optical coherence tomography. In this approach, phase-sensitive data can be recorded before and after application of a first field to induce an eddy current and block correlation algorithms can be used to compute the depth resolved strain field in the tissue resulting from the motion of the nanoparticle or metallic composition.

Ferromagnetic nanoparticles have a permanent magnetic moment, i.e. the ferromagnetic nanoparticles are magnetized. Ferromagnetic particles may be synthesized from iron with a minimum diameter is about 20-30 nm or Cobalt with a minimum diameter is about 10-12 nm. In addition ferromagnetic particles may be coated with gold as the superparamagnetic particles are coated with gold.

In this case the externally applied magnetic flux density (B) interacts with the magnetic moment in the nanoparticle and can produce either linear force or torque that induces an internal strain field in the tissue.

In exemplary embodiments, large magnetic fields can be generated by low temperature superconducting magnets. These magnets need only be "charged" once, maintained at a low temperature and do not require an external current to maintain the magnetic field.

A metallic composition can be administered to the subject. Administration of exogenous metallic compositions, for example, metallic nanoparticles is described in greater detail below. Optionally, the cell can be located within a subject and the metallic composition can be administered to the subject. Optionally, the cell can be a macrophage and at least one metallic nanoparticle can be located within the macrophage or can be connected to the macrophage. The macrophage can be located in an atherosclerotic plaque within the subject. The macrophage can also be located within the eye of the subject.

In the methods described herein, a nanoparticle comprising a material with non-zero magnetic susceptibility can be positionally moved in vivo, in vitro, or ex vivo by an applied magnetic field. A material of non-zero magnetic susceptibility can include a variety of materials. For example, the nanoparticle can comprise any physiologically tolerable magnetic material or combinations thereof. The term magnetic material can optionally include any material displaying ferromagnetic, paramagnetic or superparamagnetic properties. For example, the nanoparticles can comprise a material selected from the group consisting of iron oxide, iron, cobalt, nickel, and chromium. Metallic compositions as described throughout, including administered nanoparticles, can be magnetic. Optionally, a nanoparticle comprises iron oxide. When a nanoparticle comprises metal or magnetic materials, it can be moved while in the subject using an internally or externally applied magnetic field, as described below. Any relevant metal with non-zero magnetic susceptibility or combinations thereof can be used. Many useable metals are known in the art; however, any metal displaying the desired characteristics can be used. Nanoparticles can also comprise a combination of a material with a non-zero magnetic susceptibility and a material with a lower or zero magnetic susceptibility. For example, gold can be combined with higher magnetic susceptibility materials (e.g., iron). For example, gold coated iron can be used that still have a permanent magnetic moment, i.e. ferromagnetic. Nanoparticles can also include a polymer coating or other coating materials alone or in combination, which are electrically conductive or contain metallic atoms with a magnetic moment. Alternatively, such polymers or coating materials can be used to attach targeting ligands, including but not limited to antibodies, as described below. When used in vivo, an administered nanoparticle can be physiologically tolerated by the subject, which can be readily determined by one skilled in the art.

Nanoparticles can be solid, hollow or partially hollow and can be spherical or asymmetrical in shape. Optionally, the cross section of an asymmetric nanoparticle is oval or elliptical. As one of skill in the art will appreciate, however, other asymmetric shapes can be used. In one example, the particle can be shaped like a bacterium. A bacterium shaped particle can be used to increase the likelihood of engulfment of the particle by a macrophage. The nanoparticles can comprise shelled or multi-shelled nanoparticles. Each shell layer can be metal. A multi-shelled particle can also have one or more layers that are non-metallic. For example, the particles can be coated with sugar, polysaccharide, protein, peptide, polypeptide, amino acid, nucleic acid, and portions or fragments of each of these coating compositions. Moreover, each coating composition or portion thereof, or metal composition can fully or partially surround any other portion of a particle.

One exemplary particle comprises iron oxide and gold. The iron oxide can form a core that is surrounded partially or fully by a gold layer. Dextran can be applied to the gold layer to comprise a particle of iron, gold and dextran. Other exemplary layers can also be used. For example, a metallic core can selected based on its magnetic properties so that it can be moved in the subject by an applied magnetic force. A second metal layer can be selected based on its light absorption properties and the light absorptive characteristics of the tissue or media where the particle is located. For example, gold can be used to enhance the absorption of near infrared light by the particle in the cell. Exemplary combinations of materials for particles that can be moved by an applied magnetic force and can absorb light more than proximate tissue or cells of the subject can be selected using the principles of photothermolysis, known in the art and described below.

Figure 2A:
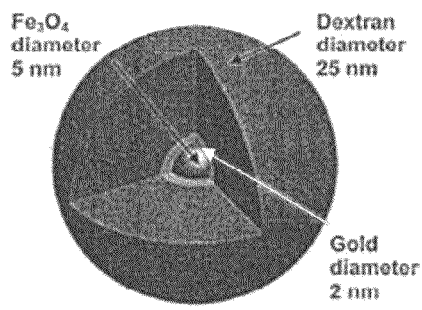
FIG. 2A is a schematic diagram showing exemplary multifunctional nanoparticles (MONs) with an iron core for magnetic properties, a gold coating to tune wavelength absorption to 700 nm (above competing plaque components such as hemoglobin), and absorbed aminodextran coating for selective macrophage uptake.
Figure 2B:
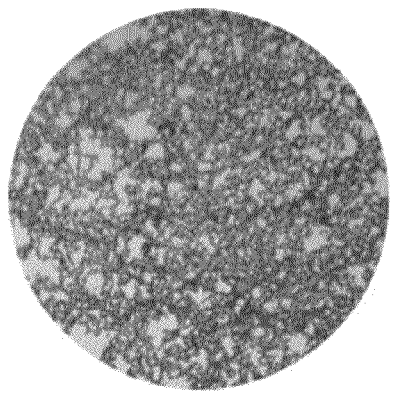
FIG. 2B is a TEM of ferromagnetic nanoparticles in absence of an external magnetic field in lattice form.

Exemplary nanoparticles are shown in FIGS. 2 and 3. FIG. 2A is a schematic diagram showing exemplary multifunctional MMUS nanoparticle with an iron core for magnetic properties, a gold coating to tune wavelength absorption to 700 nm (above competing plaque components), and an adsorbed amino-dextran coating for enhanced selective macrophage uptake. FIG. 2B is a Transmission Electron Microscope image of ferromagnetic nanoparticles in lattice form. Ferromagnetic nanoparticles include have a minimum size that is required to form a domain, i.e. for Iron ferromagnetic nanoparticles the size is about 25 nm in diameter for the iron core. Second, the ferromagnetic nanoparticles have a permanent magnetic moment that is represented by a vector. The vector can point in any direction relative to the particle.

Figure 3A:
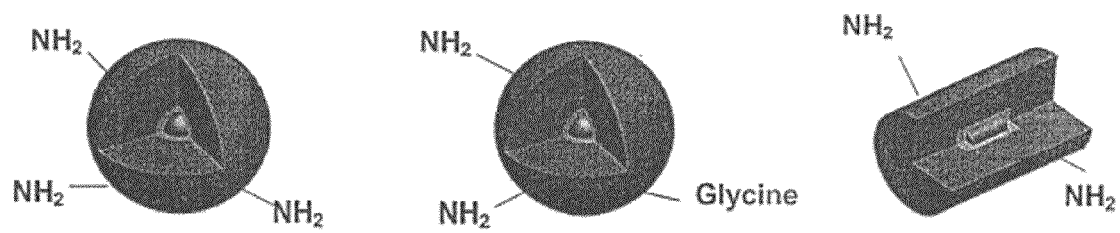
FIG. 3A is a schematic diagram showing exemplary multifunctional nanoparticles (MONs) with an aminodextran outer shell adsorbed on an inner gold shell and FIG. 3B is the molecular structure of aminodextran.
Figure 3B:
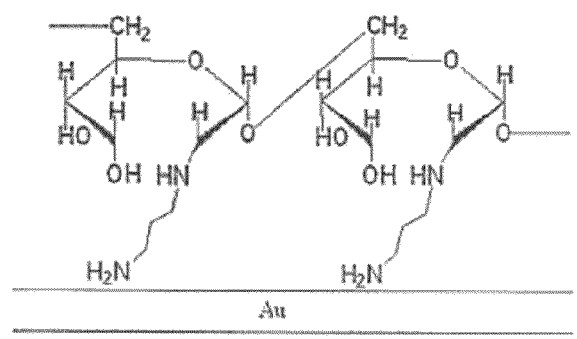

FIG. 3A is a schematic diagram showing several exemplary multifunctional MMUS nanoparticles (MONs) with an amino-dextran outer shell adsorbed on an inner gold shell. As shown in FIG. 3B, additional $NH_2$ sites on the dextran that are not bound to gold can be used to conjugate small molecules such as fluorescein isothiocyanate ("FITC"), or and Glycine to raise the selectivity for macrophage uptake. Particle shape can also be altered to mimic the rod-like appearance of bacteria to enhance macrophage uptake, as shown in FIG. 3A.

Shelled or multi-shelled nanoparticles can have targeting ligands conjugated to the shell material wherein the targeting ligand has an affinity for or binds to a target site in a subject or ex vivo. Such shelled or multi-shelled nanoparticles can be made, for example, using techniques known in the art, for example, as described in Loo et al., "Nanoshell-Enabled Photonics-Based Imaging and Therapy of Cancer," Tech. Cancer Res. and Treatment, (2004) 3(1) 33-40, which is incorporated herein by reference for the methods taught herein. Further, Oldenburg et al., "Nanoengineering of Optical Resonances," Chemical Physics Letters (1998) 288, 243-247, is incorporated herein for methods of nanoshell synthesis.

The methods of detecting cells and compositions using ultrasound can comprise administering a plurality of metallic nanoparticles to a subject.

Optionally, at least one administered nanoparticle localizes within a macrophage located in the subject. At least one administered nanoparticle can also be optionally configured to localize to a target site in the subject.

Localized Nanoparticle to a Target Site

A metallic composition, including a nanoparticle, can be configured to localize to a target site within the subject. For example, the metallic composition can be configured to localize to a neoplastic cell, to a peptide, to a protein, or to a nucleic acid. Optionally, the target site is an extracellular domain of a protein. A variety of cell types can also be targets of the metallic compositions. For example, target cells can be selected from one or more of a neoplastic cell, a squameous cell, a transitional cell, a basal cell, a muscle cell, an epithelial cell, and a mucosal cell. The target cells can also be located at different anatomical locations within a subject. For example, the cell can be located in the subject at an anatomical location selected from the group consisting of a lung, bronchus, intestine, stomach, colon, eye, heart, blood vessel, cervix, bladder, urethra, skin, muscle, liver, kidney, and blood.

One or more administered nanoparticle can localize to a desired target within the subject using passive or active targeting mechanisms. Passive targeting mechanisms take advantage of the subject's inherent defense mechanisms to highlight phagocytic cells naturally responsible for particle clearance. For example, macrophage rich areas are a pathological correlate to an unstable atherosclerotic plaque in a subject. Moreover, administered nanoparticles, for example, small superparamagnetic and ultrasmall superparamagnetic particles of iron oxide, are avidly taken up, or engulfed by, macrophages located in unstable plaques. Thus, through the subject's natural defense mechanism, wherein macrophages accumulate in an unstable atherosclerotic plaque and engulf administered nanoparticles, administered nanoparticles can passively target the unstable plaque. Similarly, macrophages located in the eye of a subject can engulf nanoparticles. Such passive targeting of nanoparticles can be used with the methods and apparatuses described herein to highlight a plaque's instability or to highlight other accumulation of phagocytic cells.

Active targeting mechanisms can refer to the use of ligand-directed, site-specific targeting of nanoparticles. A nanoparticle can be configured to localize to a desired target site in a subject using a wide variety of targeting ligands including, but not limited to, antibodies, polypeptides, peptides, nucleic acids, and polysaccharides. Such nanoparticles are referred to herein as "targeted nanoparticles." Targeting ligands or fragments thereof can be used to target a nanoparticle to cellular, or other endogenous or exogenous biomarkers in the subject. Such a biomarkers or "target sites" can include, but are not limited to, proteins, polypeptides, peptides, polysaccharides, lipids, or antigenic portions thereof, which are expressed within the subject. When active targeting mechanisms are used to target a cell, the targeted nanoparticle can be optionally internalized by the targeted cell.

Thus, using the disclosed methods, at least one administered nanoparticle can optionally localize within a macrophage located in the subject and/or at least one administered targeted nanoparticle can localize to a desired target site in the subject.

The methods and apparatuses are not, however, limited to in vivo administration to a subject. As would be clear to one skilled in the art, nanoparticles, including targeted nanoparticles, can be administered in vitro to an ex vivo sample with localization of the nanoparticle to a desired target site and subsequent imaging occurring in vitro. Moreover, a composition, including at least one nanoparticle can be administered to a subject in vivo, and a sample can be subsequently taken from the subject and imaged ex vivo using the methods, systems, and apparatuses described herein.

When using a targeted nanoparticle the target site in vivo or in vitro can be endogenous or exogenous. The target site can be selected from the group consisting of an organ, cell, cell type, blood vessel, thrombus, fibrin and infective agent antigens or portions thereof. Optionally, the target site can be a neoplastic cell. The target site can also be an extracellular domain of a protein. Furthermore, the target site can be selected from the group consisting of a lung, bronchus, intestine, stomach, colon, heart, brain, blood vessel, cervix, bladder, urethra, skin, muscle, liver, kidney and blood. The target site can also be a cell. For example, a cell can be selected from the group consisting of, but not limited to, a neoplastic cell, a squameous cell, a transitional cell, a basal cell, a muscle cell, an epithelial cell, a lymphocyte, a leukocyte, a monocyte, a red blood cell, and a mucosal cell.

Thus, targeted nanoparticles can be targeted to a variety of cells, cell types, antigens (endogenous and exogenous), epitopes, cellular membrane proteins, organs, markers, tumor markers, angiogenesis markers, blood vessels, thrombus, fibrin, and infective agents. For example, targeted nanoparticles can be produced that localize to targets expressed in a subject. Optionally, the target can be a protein, and can be a protein with an extracellular or transmembrane domain. Optionally, the target can be the extracellular domain of a protein.

Desired targets can be based on, but not limited to, the molecular signature of various pathologies, organs and/or cells. For example, adhesion molecules such as integrin $\alpha v \beta 3$, intercellular adhesion molecule-1 (I-CAM-1), fibrinogen receptor GPIIb/IIIa and VEGF receptors are expressed in regions of angiogenesis, inflammation or thrombus. These molecular signatures can be used to localize nanoparticles through the use of a targeting ligand. The methods described herein optionally use nanoparticles targeted to one or more of VEGFR2, I-CAM-1, αvβ3 integrin, αv integrin, fibrinogen receptor GPIIb/IIIa, P-selectin, and/or mucosal vascular adressin cell adhesion molecule-1.

As used, the term "epitope" is meant to include any determinant capable of specific interaction with a targeting ligand as described below. Epitopic determinants can consist of chemically active surface groupings of molecules such as amino acids or sugar side chains and can have specific three dimensional structural characteristics, as well as specific charge characteristics.

Targeting ligands specific for a molecule that is expressed or over-expressed in a cell, tissue, or organ targeted for imaging, such as pre-cancerous, cancerous, neoplastic, or hyperproliferative cells, tissues, or organs, can be used with the nanoparticles described herein. This use can include the in vivo or in vitro imaging, detection, or diagnosis of pre-cancerous, cancerous, neoplastic or hyperproliferative cells in a tissue or organ. The compositions and methods can be used or provided in diagnostic kits for use in detecting and diagnosing cancer.

As used herein, a targeted cancer to be imaged, detected or diagnosed can be selected from, but are not limited to, the group comprising lymphomas (Hodgkins and non-Hodgkins), B cell lymphoma, T cell lymphoma, myeloid leukemia, leukemias, mycosis fungoides, carcinomas, carcinomas of solid tissues, squamous cell carcinomas, adenocarcinomas, sarcomas, gliomas, blastomas, neuroblastomas, plasmacytomas, histiocytomas, melanomas, adenomas, hypoxic tumors, myelomas, AIDS-related lymphomas or sarcomas, metastatic cancers, bladder cancer, brain cancer, nervous system cancer, squamous cell carcinoma of head and neck, neuroblastoma/glioblastoma, ovarian cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, hematopoietic cancers, testicular cancer, colo-rectal cancers, prostatic cancer, or pancreatic cancer.

Pre-cancerous conditions to be imaged, detected or diagnosed include, but are not limited to, cervical and anal dysplasias, other dysplasias, severe dysplasias, hyperplasias, atypical hyperplasias, and neoplasias. As would be clear to one skilled in the art, however, additional cancers and pre-cancerous conditions can be imaged, detected or diagnosed using the methods and apparatuses described herein.

Using methods known in the art, and as described herein, targeting ligands, such as polyclonal or monoclonal antibodies, can be produced to desired target sites in a subject. Thus, a targeted nanoparticle can further comprise an antibody or a fragment thereof. Methods for preparing and characterizing antibodies are well known in the art (See, e.g., Antibodies: A Laboratory Manual, Cold Spring Harbor Laboratory, 1988; incorporated herein by reference for the methods taught therein).

Monoclonal antibodies can be obtained from a population of substantially homogeneous antibodies, i.e., the individual antibodies comprising the population are identical except for possible naturally-occurring mutations that can be present in minor amounts. Thus, the modifier "monoclonal" indicates the character of the antibody as not being a mixture of discrete antibodies.

For example, the monoclonal antibodies can be made using the hybridoma method first described by Kohler & Milstein, Nature 256:495 (1975), or can be made by recombinant DNA methods (Cabilly, et al., U.S. Pat. No. 4,816,567).

In the hybridoma method, a mouse or other appropriate host animal, such as hamster can be immunized to elicit lymphocytes that produce or are capable of producing antibodies that will specifically bind to the antigen used for immunization. Alternatively, lymphocytes can be immunized in vitro. Lymphocytes can be then fused with myeloma cells using a suitable fusing agent, such as polyethylene glycol, to form a hybridoma cell (Goding, Monoclonal Antibodies: Principles and Practice, pp. 59-103 (Academic Press, 1986)).

DNA encoding a monoclonal antibody can be readily isolated and sequenced using conventional procedures (e.g., by using oligonucleotide probes that are capable of binding specifically to genes encoding the heavy and light chains of murine antibodies). The hybridoma cells can serve as a preferred source of such DNA. Once isolated, the DNA can be placed into expression vectors, which can then be transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences, Morrison, et al., Proc. Nat. Acad. Sci. 81, 6851 (1984), or by covalently joining to the immunoglobulin coding sequence all or part of the coding sequence for a non-immunoglobulin polypeptide. In that manner, "chimeric" or "hybrid" antibodies can be prepared that have the binding specificity of an anti-cancer, pre-cancer, or hyperproliferative cell or other target molecule. Optionally, the antibody used herein is "humanized" or fully human.

Non-immunoglobulin polypeptides can be substituted for the constant domains of an antibody, or they can be substituted for the variable domains of one antigen-combining site of an antibody to create a chimeric bivalent antibody comprising one antigen-combining site having specificity for a first antigen and another antigen-combining site having specificity for a different antigen.

Chimeric or hybrid antibodies also can be prepared in vitro using known methods in synthetic protein chemistry, including those involving crosslinking agents.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature 321, 522-525 (1986); Riechmann et al., Nature 332, 323-327 (1988); Verhoeyen et al., Science 239, 1534-1536 (1988)), by substituting rodent CDRs or CDR sequences for the corresponding sequences of a human antibody. Accordingly, such "humanized" antibodies are chimeric antibodies, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Antibodies can be humanized with retention of high affinity for the target site antigen and other favorable biological properties. Humanized antibodies can be prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target site antigen(s), can be achieved. In general, the CDR residues are directly and most substantially involved in influencing antigen binding.

Human monoclonal antibodies can be made by a hybridoma method. Human myeloma and mouse-human heteromyeloma cell lines for the production of human monoclonal antibodies have been described, for example, by Kozbor, J. Immunol. 133, 3001 (1984), and Brodeur, et al., Monoclonal Antibody Production Techniques and Applications, pp. 51-63 (Marcel Dekker, Inc., New York, 1987).

Transgenic animals (e.g., mice) can be used that are capable, upon immunization, of producing a repertoire of human antibodies in the absence of endogenous immunoglobulin production. For example, it has been described that the homozygous deletion of the antibody heavy chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., Proc. Natl. Acad. Sci. USA 90, 2551-255 (1993); Jakobovits et al., Nature 362, 255-258 (1993).

Alternatively, phage display technology (McCafferty et al., Nature 348, 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S, and Chiswell, David J., Current Opinion in Structural Biology 3, 564-571 (1993). Several sources of V-gene segments can be used for phage display. Clackson et al., Nature 352, 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222, 581-597 (1991), or Griffith et al., EMBO J. 12, 725-734 (1993). In a natural immune response, antibody genes accumulate mutations at a high rate (somatic hypermutation). Some of the changes introduced can confer higher affinity, and B cells displaying high-affinity surface immunoglobulin are preferentially replicated and differentiated during subsequent antigen challenge. This natural process can be mimicked by employing the technique known as "chain shuffling" (Marks et al., Bio/Technol. 10, 779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the mM range. A strategy for making very large phage antibody repertoires (also known as "the mother-of-all libraries") has been described by Waterhouse et al., Nucl. Acids Res. 21, 2265-2266 (1993), and the isolation of a high affinity human antibody directly from such large phage library is reported by Griffith et al., EMBO J. (1994). Gene shuffling can also be used to derive human antibodies from rodent antibodies, where the human antibody has similar affinities and specificities to the starting rodent antibody. According to this method, which is also referred to as "epitope imprinting," the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT patent application WO 93/06213, published Apr. 1, 1993). Unlike traditional humanization of rodent antibodies by CDR grafting, this technique provides completely human antibodies, which have no framework or CDR residues of rodent origin.

Bispecific antibodies are monoclonal, preferably human or humanized, antibodies that have binding specificities for at least two different antigens. One of the binding specificities is for a first antigen and the other one is for a second antigen.

Traditionally, the recombinant production of bispecific antibodies is based on the coexpression of two immunoglobulin heavy chain-light chain pairs, where the two heavy chains have different specificities (Millstein and Cuello, Nature 305, 537-539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published May 13, 1993), and in Traunecker et al., EMBO 10, 3655-3659 (1991). For further details of generating bispecific antibodies see, for example, Suresh et al., Methods in Enzymology 121, 210 (1986).

Heteroconjugate antibodies are also within the scope of the described compositions and methods. Heteroconjugate antibodies are composed of two covalently joined antibodies. Heteroconjugate antibodies can be made using any convenient cross-linking methods. Suitable cross-linking agents are well known in the art, and are disclosed in U.S. Pat. No. 4,676,980, along with a number of cross-linking techniques.

A variety of immunoassay formats can be used to select antibodies that selectively bind with a desired target site or target site antigen. For example, solid-phase ELISA immunoassays are routinely used to select antibodies selectively immunoreactive with a protein, protein variant, or fragment thereof. See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem., 107:220 (1980).

Not only can a targeted nanoparticle comprise an antibody or fragment thereof, but a targeted nanoparticle can also comprise targeting ligand that is a polypeptide or a fragment thereof. Optionally, polypeptides that are internalized by target cells can be attached to the surface of a nanoparticle. Ligands that are internalized can optionally be used for internalization of a nanoparticle into a target cell. A modified phage library can be use to screen for specific polypeptide sequences that are internalized by desired target cells. For example, using the methods described in Kelly et al., "Detection of Vascular Adhesion Molecule-1 Expression Using a Novel Multimodal Nanoparticle," Circulation Res., (2005) 96:327-336, which is incorporated herein for the methods taught therein, polypeptides can be selected that are internalized by VCAM-1 expressing cells or other cells expressing a ligand of interest.

There are a number of methods for isolating proteins which can bind a desired target. For example, phage display libraries have been used to isolate numerous polypeptides that interact with a specific target. (See for example, U.S. Pat. Nos. 6,031,071; 5,824,520; 5,596,079; and 5,565,332 which are herein incorporated by reference at least for their material related to phage display and methods related to combinatorial chemistry). Thus targeted nanoparticles can comprise a polypeptide or fragments thereof that interact with a desired target. A targeted nanoparticle can also comprise a binding domain of an antibody or phage.

The term "polypeptide" or "peptide" is used broadly herein to mean two or more amino acids linked by a peptide bond. The term "fragment" or "proteolytic fragment" also is used herein to refer to a product that can be produced by a proteolytic reaction on a polypeptide, i.e., a peptide produced upon cleavage of a peptide bond in the polypeptide. A fragment can be produced by a proteolytic reaction, but it should be recognized that a fragment need not necessarily be produced by a proteolytic reaction but can be produced using methods of chemical synthesis or methods of recombinant DNA technology, to produce a synthetic peptide that is equivalent to a proteolytic fragment. It should be recognized that the term "polypeptide" is not used herein to suggest a particular size or number of amino acids comprising the molecule, and that a polypeptide can contain up to several amino acid residues or more.

A nanoparticle can bind selectively or specifically to a desired target site, and/or can be internalized by a target cell. Such selective or specific binding and/or internalization can be readily determined using the methods, systems and apparatuses described herein. For example, selective or specific binding can be determined in vivo or in vitro by administering a targeted nanoparticle and detecting an increase in light scattering from the nanoparticle bound to a desired target site or internalized into the desired target cell. Detection of light scattering can be measured using the systems and apparatuses described below.

Thus, a targeted nanoparticle can be compared to a control nanoparticle having all the components of the targeted nanoparticle except the targeting characteristics, such as, for example, targeting ligand. By detecting phase sensitive image data from the targeted nanoparticle bound to a desired target site versus a control nanoparticle, the specificity or selectivity of binding or internalization can be determined. If an antibody, polypeptide, or fragment thereof, or other targeting ligand is used, selective or specific binding to a target can be determined based on standard antigen/polypeptide/epitope/antibody complementary binding relationships. Further, other controls can be used. For example, the specific or selective targeting of the nanoparticles can be determined by exposing targeted nanoparticles to a control tissue, which includes all the components of the test or subject tissue except for the desired target ligand or epitope. To compare a control sample to a test sample, levels of light scattering can be detected by, for example, the systems described below and the difference in levels or location can be compared.

A targeting ligand can be coupled to the surface or shell of at least one of the nanoparticle. Targeted nanoparticles comprising targeting ligands can be produced by methods known in the art. For example ligands, including but not limited to, antibodies, peptides, polypeptides, or fragments thereof can be conjugated to the nanoparticle surface.

Any method known in the art for conjugating a targeting ligand to a nanoparticle can be employed, including, for example, those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982). Established protocols have been developed for the labeling metallic nanoparticles with a broad range of biomolecules, including protein A, avidin, streptavidin, glucose oxidase, horseradish peroxidase, and IgG (antibodies). Nanoparticles can be prepared with bioorganic molecules on their surface (DNA, antibodies, avidin, phospholipids, etc). The nanoparticles can be characterized, modified, and conjugated with organic and biomolecules. Polymers or other intermediate molecules can be used to tether antibodies or other targeting ligands to the surface of nanoparticles. Methods of tethering ligands to nanoparticles are know in the art as described in, for example, Loo et al., "Nanoshell-Enabled Photonics-Based Imaging and Therapy of Cancer," Tech. Cancer Res. and Treatment, (2004) 3(1) 33-40, which is incorporated herein by reference for the methods taught herein.

Covalent binding of a targeting ligand to a nanoparticle can be achieved, for example, by direct condensation of existing side chains or by the incorporation of external bridging molecules. Many bivalent or polyvalent agents can be useful in coupling polypeptide molecules to other particles, nanoparticles, proteins, peptides or amine functions. Examples of coupling agents are carbodiimides, diisocyanates, glutaraldehyde, diazobenzenes, and hexamethylene diamines. This list is not intended to be exhaustive of the various coupling agents known in the art but, rather, is exemplary of the more common coupling agents that can be used.

Optionally, one can first derivatize an antibody if used, and then attach the nanoparticle to the derivatized product. As used herein, the term "derivatize" is used to describe the chemical modification of the antibody substrate with a suitable cross-linking agent. Examples of cross-linking agents for use in this manner include the disulfide-bond containing linkers SPDP (N-succinimidyl-3-(2-pyridyldithio)propionate) and SMPT (4-succinimidyl-oxycarbonyl-α-methyl-α (2-pyridyldithio)toluene).

Targeting ligands can also be conjugated to nanoparticles using methods including the preparation of biotinylated antibody molecules and their consequent interaction with streptavidin/nanoparticle conjugates. This approach takes advantage of strong biospecific interaction between biotin and streptavidin and known protocols for immobilization of streptavidin on nanoparticles. Polypeptides with thiol terminated alkyl chains can be directly attached to the surface of nanoparticles using the procedures described in Elghanian, R., et al., Selective colorimetric detection of polynucleotides based on the distance-dependent optical properties of gold nanoparticles. Science, 1997. 277(5329): p. 1078-1080 (incorporated by reference for the methods taught therein). For conjugation procedure one can use a mixture of thiol terminated polypeptides and relatively small mercaptoacetic molecules to avoid high density immobilization of the polypeptides.

Targeted nanoparticles can be prepared with a biotinylated surface and an avidinated antibody, peptide, polypeptide or fragment thereof can be attached to the nanoparticle surface using avidin-biotin bridging chemistry. Avidinated nanoparticles can be used and a biotinylated antibody or fragment thereof or another biotinylated targeting ligand or fragments thereof can be administered to a subject. For example, a biotinylated targeting ligand such as an antibody, protein or other bioconjugate can be used. Thus, a biotinylated antibody, targeting ligand or molecule, or fragment thereof can bind to a desired target within a subject. Once bound to the desired target, the nanoparticle with an avidinated surface can bind to the biotinylated antibody, targeting molecule, or fragment thereof. When bound in this way, light energy can be transmitted to the bound nanoparticle, which can produce light scattering of the transmitted light. An avidinated nanoparticle can also be bound to a biotinylated antibody, targeting ligand or molecule, or fragment thereof prior to administration to the subject.

When using a targeted nanoparticle with a biotinylated surface or an avidinated surface a targeting ligand can be administered to the subject. For example, a biotinylated targeting ligand such as an antibody, polypeptide or other bioconjugate, or fragment thereof, can be administered to a subject and allowed to accumulate at a target site When a targeted nanoparticle with a biotinylated surface is used, an avidin linker molecule, which attaches to the biotinylated targeting ligand can be administered to the subject. Then, a targeted nanoparticle with a biotinylated shell can be administered to the subject. The targeted nanoparticle binds to the avidin linker molecule, which is bound to the biotinylated targeting ligand, which is itself bound to the desired target. In this way, a three step method can be used to target nanoparticles to a desired target. The targeting ligand can bind to all of the desired targets detailed above as would be clear to one skilled in the art.

Nanoparticles, including targeted nanoparticles, can also comprise a variety of markers, detectable moieties, or labels. Thus, for example, a nanoparticle equipped with a targeting ligand attached to its surface can also include another detectable moiety or label. As used herein, the term "detectable moiety" is intended to mean any suitable label, including, but not limited to, enzymes, fluorophores, biotin, chromophores, radioisotopes, colored particles, electrochemical, chemical-modifying or chemiluminescent moieties. Common fluorescent moieties include fluorescein, cyanine dyes, coumarins, phycoerythrin, phycobiliproteins, dansyl chloride, Texas Red, and lanthanide complexes. Of course, the derivatives of these compounds are included as common fluorescent moieties.

The detection of the detectable moiety can be direct provided that the detectable moiety is itself detectable, such as, for example, in the case of fluorophores. Alternatively, the detection of the detectable moiety can be indirect. In the latter case, a second moiety reactable with the detectable moiety, itself being directly detectable can be employed.

A composition, including at least one nanoparticle, can be administered to a subject orally, parenterally (e.g., intravenously), by intramuscular injection, by intraperitoneal injection, transdermally, extracorporeally, topically or the like. Parenteral administration of a composition, if used, is generally characterized by injection. Injectables can be prepared in conventional forms, either as liquid solutions or suspensions, solid forms suitable for solution of suspension in liquid prior to injection, or as emulsions.

The compositions, including nanoparticles, can be used in combination with a pharmaceutically acceptable carrier. By "pharmaceutically acceptable" is meant a material that is not biologically or otherwise undesirable, i.e., the material can be administered to a subject, along with the nanoparticle, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5.0 to about 8.0, and more preferably from about 7.0 to about 7.5. As described above, compositions can be administered intravascularly. Administered compositions can include carriers, thickeners, diluents, buffers, preservatives, surface active agents and the like in addition to the composition of choice. Administered compositions can also include one or more active ingredients such as antimicrobial agents, anti-inflammatory agents, anesthetics, and the like.

When used in the described methods, an effective amount of one of the compositions, including the nanoparticles, can be determined by one skilled in the art. The specific effective dose level for any particular subject can depend upon a variety of factors including the type and location of the target site, activity of the specific composition employed, the specific composition employed, the age, body weight, general health, sex and diet of the subject, the time of administration, the route of administration, the rate of excretion of the specific composition employed, the duration of the treatment, drugs used in combination or coincidental with the specific composition employed, and like factors well known in the medical arts. For example, it is well within the skill of the art to start doses of the composition at levels lower than those required to achieve the desired diagnostic or imaging effect and to gradually increase the dosage until the desired effect is achieved. If desired, an effective dose can be divided into multiple doses for purposes of administration.

Depending on the exemplary factors above, on the composition used, on the intended target site for the composition, and whether active or passive targeting of the described compositions is used, the time between administration of the described compositions and the detection of the described nanoparticles within the subject can vary. For example, detection of the described nanoparticles can be performed at one or more time seconds, minutes, hours, days, and/or weeks after administration of the compositions to the subject. When and how frequently methods of detection of an administered composition are performed can be determined by one skilled in the art through routine administration and detection.

The described methods can be used to a detect cell. In some examples, the cell can be a macrophage that has engulfed a metallic particle or composition. The macrophage can be located anywhere in a subject, for example, in the eye or in a vulnerable plaque. In other examples, the cell can be a cancer cell, wherein a metallic particle has been targeted to the cell. A cancer cell can be targeted anywhere in the subject. In other examples, the cell can be any cell of a subject that has been targeted with a metallic particle.

EXAMPLES

The following examples are put forth so as to provide those of ordinary skill in the art with a complete disclosure and description of how the compositions, compositions, articles, devices, systems, and/or methods claimed herein are made and evaluated, and are intended to be purely exemplary and are not intended to limit the scope of compositions, compositions, articles, devices, systems, and/or methods. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Superparamagnetic Iron Oxide (SPIO) Nanoparticles

Colloidal suspensions of SPIO nanoparticles, Ferumoxides or AMI-25 with the trade name Feridex® I.V. (Advanced Magnetics, Cambridge, Mass., USA) are approved by the United States Food and Drug Administration (FDA) for human use in 1997. The SPIO nanoparticles consisted of nonstoichiometric magnetite cores, iron, and a dextran T-10 coating added to prevent aggregation and facilitate stabilization in the liver. The mean core diameter and volume mean diameter measured by laser light scattering of these nanoparticles were 20 and 80 nm, respectively. Peak concentrations of SPIO nanoparticles in the liver were observed 1 h after an intravenous injection (18 µmol Fe/kg body weight). The uptake of SPIO nanoparticles by macrophage cells is directly proportional to the IV concentration, blood half-life, and their core size.

Experimental Preparation

Figure 4:
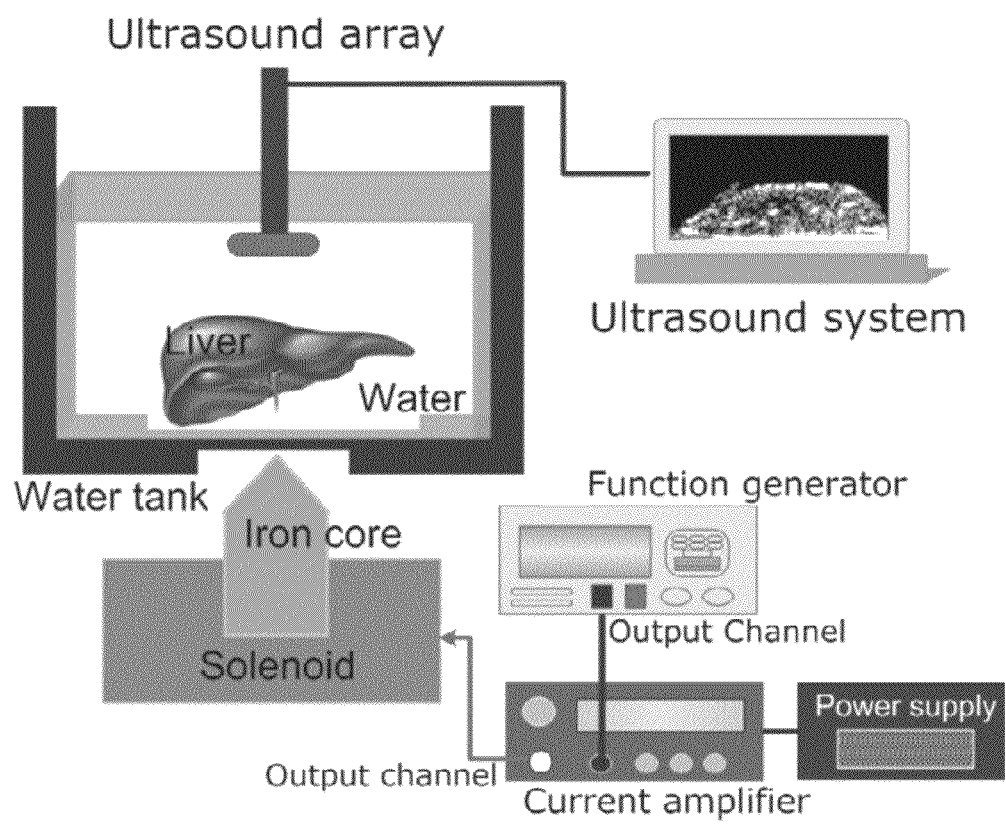
FIG. 4 is a schematic diagram of the setup with the magnetic field generator and conical iron core inside the solenoid.

As shown in FIG. 4, a schematic diagram of the apparatus is shown. A liver sample was placed into a small rectangular plastic container (10 cm 10 cm) filled with water to provide acoustic coupling between the ultrasonic transducer and the specimen. The sample was imaged from the top using a linear array transducer (128 Channel). Magnetic excitation of the sample was provided by the solenoid positioned below at the bottom surface of the water tank. The distance between the liver specimens and iron core tip was about 1.5 mm, and the magnetic field strength at this distance was measured using a tesla-meter to observe the correlation between the magnetic field strength and the ultrasound measurement.

The magnetic generator comprises a solenoid (Ledex 6EC, Saia-Burgess Inc., USA), a function generator (HP 33120A, Hewlett Packard Inc., USA), a current amplifier, and a regulated DC power supply. A finite element method (FEM, Maxwell SV, Ansoft Inc., USA) was used to design the magnetic field generator and evaluate the magnetic flux density in response to a time-varying input sinusoidal current signal. The conical iron core may be positioned close to the bottom surface of the water tank as possible while ensuring no physical contact, as to maximize the magnetic field strength applied to liver specimens. The FEM calculations and teslameter measurements were consistent and indicated that the maximum magnetic field strength used in this experiment was approximately 2 T at a distance of 1.5 mm from the tip of the iron core. The FEM calculation also demonstrated that an iron core inserted in the centre of solenoid dramatically increased and better localized the magnetic field strength at the liver specimens. Magnetic field distributions from the FEM simulation showed that the maximal and principal direction of the magnetic field strength at the liver specimen was along the z-direction due to the conical iron core.

Ultrasound experiments were performed ex vivo using an ultrasound imaging system (Sonosite 180 Plus, Sonosite Inc., USA) equipped with a 38 mm aperture, broadband (10-5 MHz) linear array transducer. The liver specimens were imaged in color power Doppler, power Doppler, M-mode and B-scan modes. B-scan sonogram images, also called the greyscale mode, are the typical ultrasound method to monitor or examine the human body using backscattering of acoustic waves. M-mode ultrasound employs a sequence of scans at a fixed ultrasound beam over a given time period. M-mode is used for visualizing rapidly moving subjects such as heart valves. Compared to conventional B-scan images, Doppler ultrasound is used to assess changes in the frequency of reflected acoustic waves. Color power Doppler converts reflected acoustic waves that are Doppler shifted into colors that overlay the conventional B-scan images and can indicate the speed and direction of moving objects. Power Doppler ultrasound is most commonly used to evaluate moving objects and has higher sensitivity than the color power Doppler mode. The gain of the color power and Doppler imaging mode may be manually adjusted to suppress the background noise. To make objective comparisons, the experimental settings of the ultrasound instrumentation were unchanged for all specimens imaged.

Results

The leftmost column of FIGS. 5(a)-(e) depicts the conventional-scan images of intact livers from mice administered 1.5, 1.0, 0.5, and 0.1 (mmol Fe/kg body weight) of SPIO nanoparticles, and the control specimen, respectively. These images do not indicate any significant differences between iron-laden and control livers. In these and all other images, the ultrasound probe was positioned near the top of the liver specimens. Conventional B-scan images were obtained prior to applying the magnetic field. In color power Doppler mode, a focused magnetic field (2 T) was applied. The liver with high dose administration of SPIO (f) shows significant increasing color Doppler signal while the normal liver (j) does not exhibit any appreciable color Doppler signal. The M-mode signal intensity and displacement are proportional to the concentration of SPIO dose. The M-mode signal obtained from a high dose specimen (k) clearly demonstrates a sinusoidal pattern of the displacement once the magnetic field is turned on.

Figure 5:
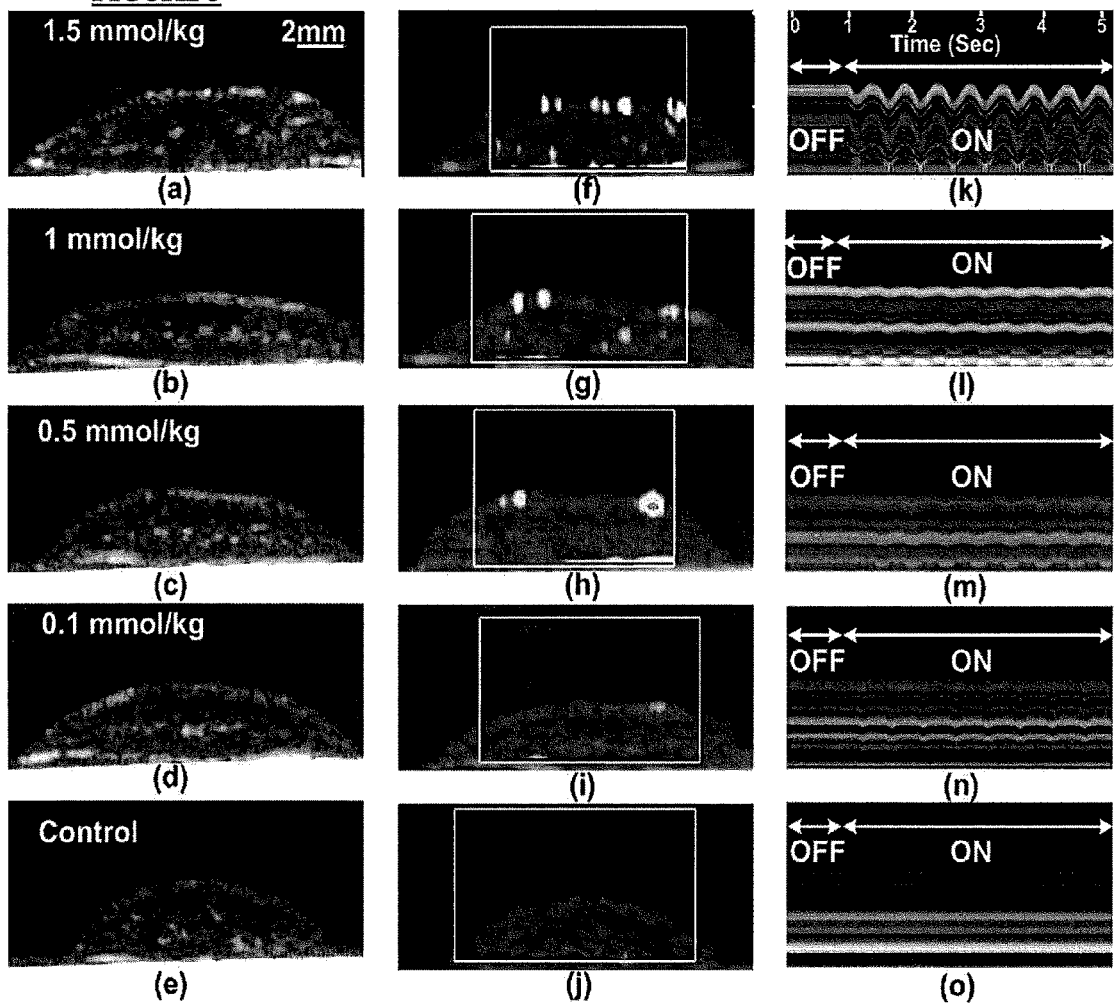
FIGS. 5(a)-(e) are ultrasound grayscale images.
FIGS. 5(f)-(j) are color power Doppler images.
FIGS. 5(k)-(o) M-mode images of livers with different SPIO doses (1.5, 1.0, 0.5, and 0.1 mmol Fe/kg and control liver).

FIGS. 5(f)-(j) shows color power Doppler images obtained from the same livers as depicted in FIGS. 2(a)-(e), correspondingly. These color power Doppler images were obtained while a 40 Hz, 20 peak-to-peak volts (Vpp) sinusoidal input was applied using a solenoid positioned below the surface of the water tank. The peak magnetic field strength was about 2 T at the specimen as measured by a tesla-meter. The field of view in color power Doppler images (the rectangular window in FIGS. 5 (a)-(e)) was centered relative to both the tip of the solenoid iron core and the liver specimens. Compared to lower dose liver specimens, the high dose (1.5 mmol Fe/kg) specimen shows progressively larger areas of Doppler signal, thus allowing the detection of tissue-based macrophages. No significant Doppler signal was observed in the control liver specimen, as shown in FIG. 5(j).

FIGS. 5(k)-(o) display M-mode measurements obtained from the corresponding liver specimens. The horizontal X-axis in these images represents the total running time (5 s) with an 'on-and-off' applied sinusoidal magnetic field (1 Hz, 20 Vpp; Bmax=1.5 T) while the Y-axis shows the vertical displacement in liver specimens, respectively. The M-mode signal intensity and displacement at the centre position of the liver specimens increased with SPIO concentration in the liver specimens. A high dose specimen (k) in the M-mode signal, for instance, clearly displays movement at twice the frequency of the applied magnetic field; no significant displacement was observed in the control liver specimen (FIG. 5(o)).

Figure 6:
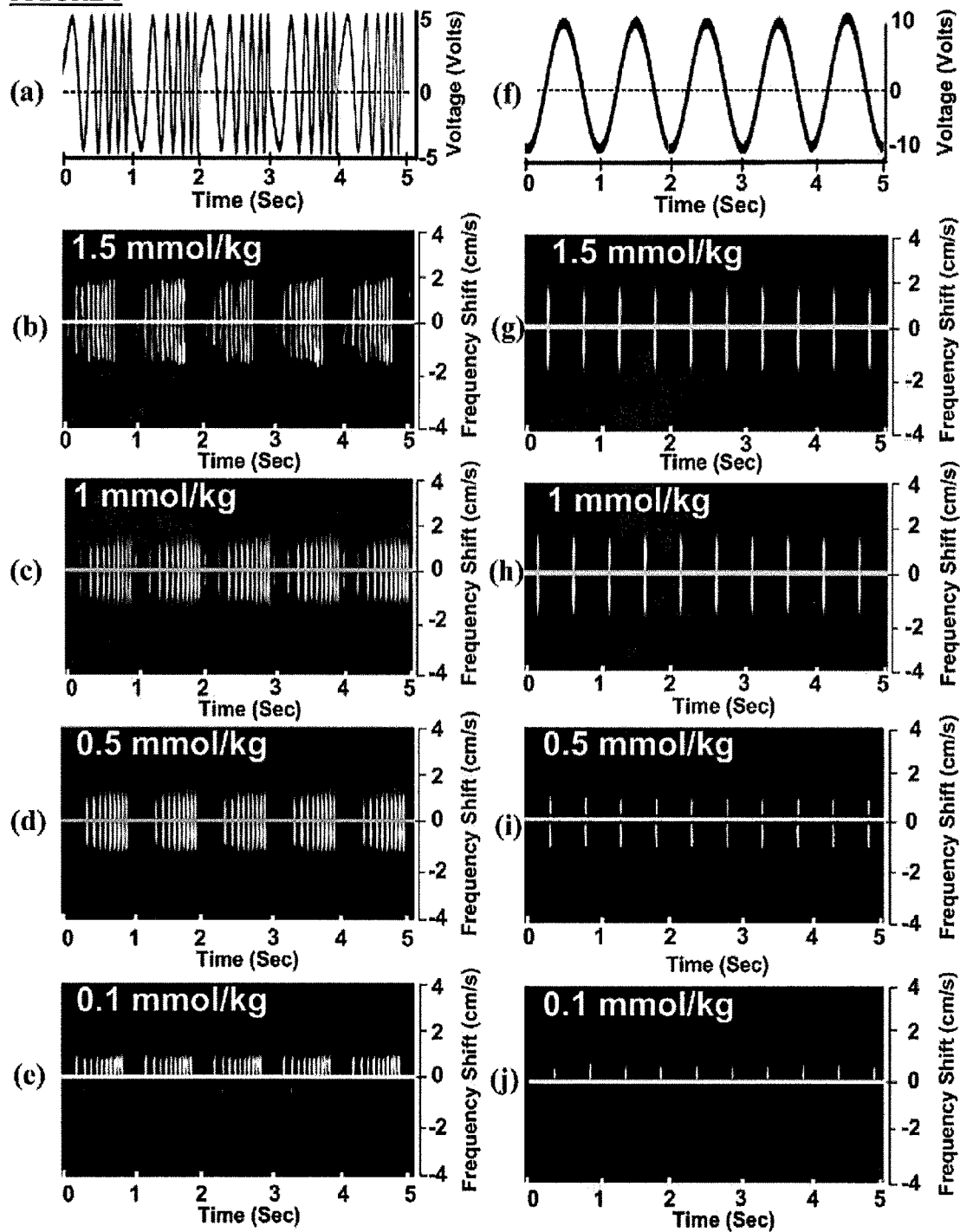
FIGS. 6(a)-(j) are graphs of the Doppler shift measured in liver specimens with different SPIO doses (1.5, 1.0, 0.5, and 0.1 mmol Fe/kg) using swept frequency input ((a)-(e)) and 1 Hz sinusoidal input ((f)-(j)).

FIG. 6 shows the Doppler shift from livers with different SPIO doses; 1.5, 1.0, 0.5, and 0.1 mmol Fe/kg and a control liver, respectively. FIG. 6(a) shows the Doppler shift while the input signal to the solenoid is a swept frequency ranging from 1 to 10 Hz over 1 s. FIG. 6(b)-(e) indicate a slight decrease in Doppler frequency shift with decreasing concentration of SPIO doses in liver specimens when a swept frequency input signal is applied. FIG. 6(f) is the input signal of a sinusoidal magnetic field at 1 Hz, 20 Vpp over 5 s. The frequency response of different liver specimens was twice that of the applied signal; this result agrees with equation (3) and can also be observed in M-mode measurements, as shown in FIGS. 5(k)-(o). When a 1 Hz sinusoidal frequency input signal is applied over a 5 s period, ten peak Doppler frequency shifts are observed over 5 s. The magnitude of the peak frequency shift scales with SPIO dose. No significant displacement of SPIO nanoparticles was observed in the saline-injected control specimens.

Example 2

FIGS. 7a-f demonstrate the Doppler shift in response to an applied magnetic field in a liver specimen with a 1 mmol Fe/kg dose. The Doppler shift measurement used in this study was measured by the positive maximum frequency using Matlab software (MathWorks, USA). The frequency of the Doppler shift was exactly twice that of the modulated frequency in all data. In all experiments, the peak Doppler shift pattern exhibits a periodicity at exactly twice the frequency of the applied signal.

Example 3

Figure 8A:
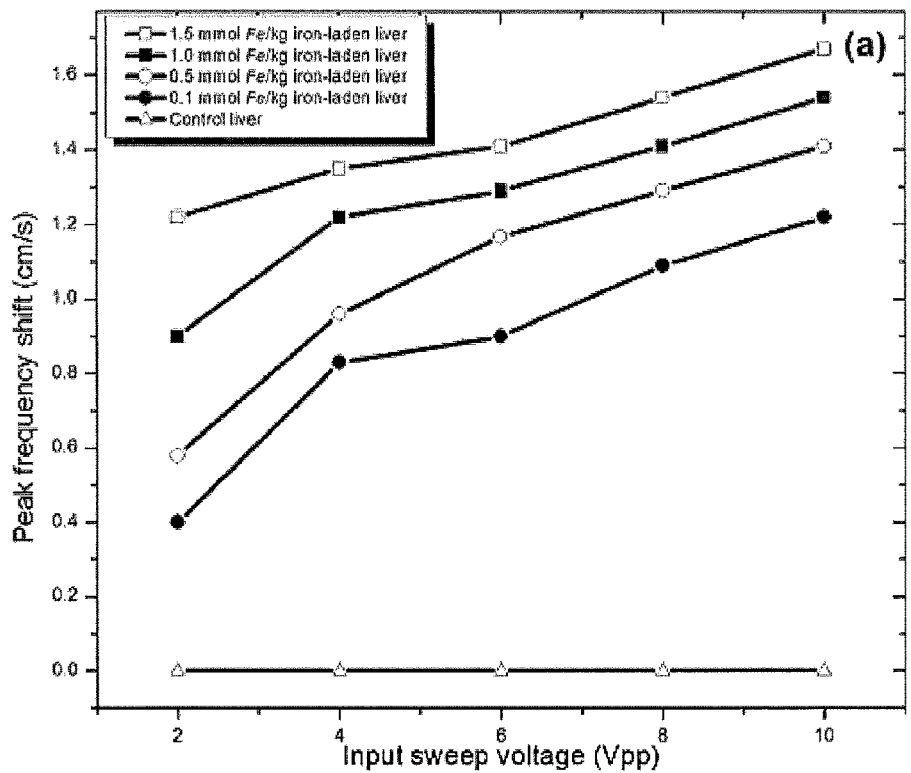
FIG. 8A is a graph of the peak frequency shift in livers with different SPIO doses (1.5, 1.0, 0.5, and 0.1 mmol Fe/kg and control) when applying a swept frequency input (1-10 Hz) with different input voltages (2-10 Vpp)

FIG. 8(a) shows the peak Doppler frequency shift in response to a swept frequency input (1-10 Hz) in liver specimens with various SPIO dose. The inset plot, as shown in FIG. 8(b), shows the peak magnetic flux density versus voltage (Vpp: peak-to-peak volts) of the input signal. The movement of iron-laden tissues depends directly upon the SPIO dose and strength of the applied magnetic field. The maximum frequency shift in all specimens was observed when the magnetic field strength was 1.85 T. No significant displacement was observed in control liver specimens.

SPIO nanoparticles are identified in histological sections as blue granules from the Prussian blue stain of control and-iron-laden mouse livers, as shown in FIG. 9. Compared to the controls, FIG. 9(a), the iron-laden specimens (1.5 mmol Fe/kg bodyweight) show significant discrete granular iron accumulations evenly distributed in observed areas, as shown in FIG. 9(b). Although intracellular iron was also observed in the control specimens, this natural iron was homogeneous rather than appearing indiscrete granular shapes. The total SPIO iron area was 5% of the histology image as calculated by Image-Pro PLUS 5.1 software (MediaCybernetics Inc., USA).

Example 4

Ferromagnetic Nanoparticles

In case of ferromagnetic nanoparticles, the frequency of the tissue displacement is that same as the frequency of the applied magnetic field and not twice as in the case of superparamagnetic nanoparticles. Ultrasound detection and methods are the same as indicated previously. Alternatively, the ferromagnetic nanoparticles have a permanent dipole moment, and application of sound energy via ultrasound transducer may provide increased detection of the ferromagnetic nanoparticles via ultrasound detection.

SPIO nanoparticles taken up by macrophages in liver are detected by magneto-motive ultrasound (MM-US) and application of a time-varying magnetic field produced microscale displacement of iron-laden macrophage cells. Detecting macrophages in iron-laden tissue by combining an external high intensity focused magnetic field provides increased detection by Doppler ultrasound. The physiological variation in the measured Doppler shift, nanoparticle concentration, and other quantities of interest may be varied to optimize the parameters of MM-US.

The detection of magnetic nanoparticles in brain tumors using high resolution intraoperative ultrasound, and improved tumor definition in recorded images may be possible. And the use of a B-scan image analysis using a 'mean grayscale' to investigate the contrast enhancement of silica nanospheres (100 nm) in mice liver may be possible. Although these results, which utilized B-mode images without an externally applied field, might hold potential for imaging brain cancer and liver, they may provide sufficient contrast enhancement for molecular imaging. The average grayscale values for the B-scan image histograms of liver samples were 41, 38, 37, 35, and 31, respectively, as shown in FIGS. 5(a)-(e)). The average brightness of the lower dose B-scan images decreased slightly with lower SPIO concentration. Conversely, the ultrasound reflective signal increased slightly with higher SPIO doses. Since the distinctions of grayscale values between the iron-laden and control samples were not noteworthy and would depend on the clinician's assessment, a better approach is sought after demonstrating contrast enhancement in conventional B-scan images.

Figure 7:
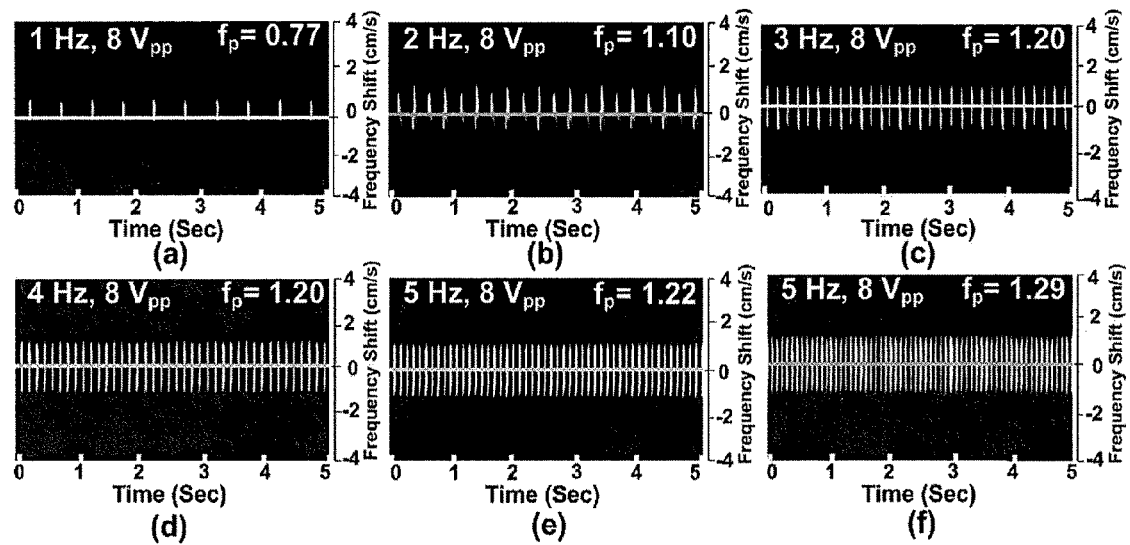
FIGS. 7(a)-(f) is the Doppler shift from liver specimens (1.0 mmol Fe/kg) with constant (8 Vpp) amplitude sinusoidal input.

To evaluate the magnetic force acting on the SPIO nanoparticles causing displacement of iron-laden tissue it becomes:

$$F = -\nabla U = \nabla\left(\frac{x_s V}{2\mu_0}|B|^2\right) = x_s V \nabla\left(\frac{|B|^2}{2\mu_0}\right) \quad (1)$$

where $\chi_s$, $V$ are the susceptibility and volume of magnetic nanoparticles and $B$, $\mu_0$ are the magnetic field strength and permeability, respectively. In our study, we applied a sinusoidal magnetic field strength principally along the z-direction. Hence, we write $\vec{B}(x, y, z; t) = \sin(2\pi f_n t) B_z(z)\hat{k}$ and the total force $F_z$ acting on the magnetic nanoparticles in the z-direction is given by $$\sum F_z = m\frac{\partial^2 z(t)}{\partial t^2} = F_m - kz(t) - r\frac{\partial z}{\partial t} \quad (2)$$

$$\sum F_z = \frac{x_s V_s}{2\mu_0}\left[1 - \cos(4\prod f_n t)B_z(z)\frac{\partial B_z}{\partial z} - kz(t) - r\frac{\partial z}{\partial t}\right] \quad (3)$$

where $F_m$ is magnetic force, $f_n$ is the modulation frequency of the applied sinusoidal magnetic field, $-kz(t)$ is an elastic restoring force, and $r(\partial z/\partial t)$ is a viscous drag force. Equation (3) confirmed that the frequency response of the force acting on the SPIO nanoparticles is exactly twice the externally applied modulation frequency, $f_n$. Accordingly, the frequency response of the ultrasound Doppler shift from the iron-laden tissue was exactly twice the modulation frequency (FIGS. 5-7). The frequency doubling feature may be utilized to eliminate unwanted frequency components that arise due to environmental noise and biological motion artifacts. The Doppler shift from tissue specimens was correlated with both the concentration of SPIO nanoparticles and the magnetic field strength. The concentration of SPIO nanoparticles was linearly proportional to the Doppler shift in iron-laden macrophage cells. Increasing the magnetic field strength increases the Doppler shift of iron-laden macrophage cells (FIGS. 5-7). In our experiment, the SPIO nanoparticles taken up by macrophages were abundant and relatively evenly distributed in the histological images.

MM-US Application to Molecular Imaging, Diagnostics, and Treatments

The role of SPIO nanoparticles as contrast agents can be expanded from the diagnosis of hepatic metastases to agents that target an inflammatory response in several diseases, particularly in atherosclerosis and tumors. Macrophages are cells associated with a response to inflammation and degenerative disorders with high phagocytic activity; therefore, imaging of macrophages may be useful to characterize diseased tissue in clinical practice. The utilization of magneto-motive ultrasound is applicable to intravascular ultrasound (IVUS) using a high frequency transducer by injection of smaller nanoscale particles, such as ultra small SPIO (US-PIO) or monocrystalline iron-oxide nanoparticles (MION), to identify macrophages as a marker of inflammation. As shown in FIG. 10, the ultrasonic transducer can be coupled with a probe 210 for intravascular detection of diseased tissue 200 associated with macrophages with nanoparticles 212. The probe can be a catheter-like endoscopic probe, which can be located within a subject to allow sound reflection off of subject tissues or nanoparticles to obtain optical measurements, medical diagnosis, treatment, and the like. Alternatively, the probe 210 may be coupled with an Optical Coherence Tomography probe, such as a rotating catheter tip including, a turbine-type catheter as described in Patent Cooperation Treaty application PCT/US04/12773 filed Apr. 23, 2004 which claims priority to U.S. provisional application 60/466, 215 filed Apr. 28, 2003; or a rotating optical catheter tip as described in U.S. patent application Ser. No. 11/551,684, which claims priority to U.S. provisional application 60/728, 48; or a rotating catheter probe as described in U.S. patent application Ser. No. 11/551,684; or an OCT-IVUS Catheter for Concurrent Luminal Imaging, U.S. provisional application 60/949,472, filed Jul. 12, 2007; each herein incorporated by reference for the methods, apparatuses and systems taught therein. The OCT probe can expose the metallic nanoparticle to light energy whereby the nanoparticle absorbs the light energy to generate an acoustic wave that is detected by the ultrasound transducer. Alternatively, the OCT probe can image the nanoparticle by OCT methods and systems.

The smaller USPIO and MION (hydrodynamic size: 15-30 nm) have a longer intravascular blood half-life, between 24 h and 36 h, and increased relative stability due to dextran coating; therefore, these nanoparticles be taken up by macrophages in atherosclerotic vulnerable plaque and malignant tumors. Combining magneto-motive excitation with Magnetic Generator 90 with high frequency detection such as ultrasound biomicroscopy (UBM; 40-200 MHz operation frequency) or scanning acoustic microscopy (SAM; 200 MHz operation frequency) may provide a dramatic increase in resolution over conventional clinical diagnostic ultrasound scanners. Identify vulnerable plaque and cancer cells using magneto-motive techniques by injection of different diameter nanoparticles and dosages can be applied as indicated by parent applications U.S. patent application Ser. No. 11/620, 562, and U.S. patent application Ser. No. 11/441,824.

Finally, molecular imaging by magneto-motive ultrasound (MM-US) is valuable for therapy treatments. A magnetic field, for example, might be used to induce magnetic hyperthermia to destroy cancer cells in surrounding tissues, as indicated in parent U.S. patent application Ser. No. 11/784, 477 where the magnetic field can destroy cells by exposing the nanoparticle to sufficient energy to heat the cell and kill the cell. Alternatively, MM-US can be coupled to a light energy source via an OCT probe as previously described to heat the nanoparticle via light energy and cause photothermolysis to heat and kill the cell.

The system can further comprise an energy source for heating the metallic particle or composition. The source can provide energy for heating the composition that is sufficient to kill or lethally injure the detected cell. In some exemplary aspects, the system can further comprise an energy source for causing a non-lethal change in the cell. For example, the energy source for causing a non-lethal change in the cell can produce a magnetic field. The energy source for causing a non-lethal change in the cell can also produce light or sound. The energy source for causing the non-lethal change in the cell and the energy source for heating the metallic particle can be of the same type. For example, each energy source can generate and/or transmit sound energy. In some exemplary aspects, the energy source for causing the non-lethal change in the cell and the energy source for heating the metallic particle are the same source. In other exemplary aspects, the energy source for causing the non-lethal change in the cell and the energy source for heating the metallic particle are different sources and/or different types of energy. For example, the energy sources for causing the non-lethal change can generates and/or transmit magnetic filed energy and the energy source for causing the heating can generate and/or transmits light energy. Thus, in some exemplary aspects the systems described herein can comprise at least three separate sources of energy. One source of energy can be the magnetic energy used for MM-US imaging, as described previously. Such magnetic energy can be referred to as imaging magnetic energy. A second source can be used to produce energy to cause heating of the metallic composition comprised by the cell to kill or lethally injure the cell. Such sources can increase the temperature of a metallic particle in the cell. For example, any source that can increase the particle temperature can be used. Exemplary sources include light energy sources and magnetic force generators that can cause an increase in temperature of the particle by inducing movement of the particle. Such sources to cause lethal changes in a cell can comprise magnetic fields, light, sound and any other energy that can cause lethal changes to a cell.

Alternatively, light energy used for the OCT imaging as would be known to one skilled in the art. Such light energy can be referred to as imaging light energy. A second source can be used to produce energy to causes a change in a cell. Such sources to cause changes in a cell can comprise sources that generate magnetic fields, light, sound and any other energy that can cause an OCT detectable change in a cell. A third source of energy can be used to produce energy to cause heating of the metallic composition comprised by the cell to kill or lethally injure the cell. Such sources can increase the temperature of a metallic particle in the cell. For example, any source that can increase the particle temperature can be used. Exemplary sources include light energy sources and magnetic force generators that can cause an increase in temperature of the particle by inducing movement of the particle. As described above, less than there sources can be also be used. For example, two sources of energy can be used. In this example, light energy for imaging can be produced by the OCT imaging modality and cell changing and killing energy can be generated by a second energy source, which can also be light energy.

Light energy can be generated by a light source for killing a cell. The light energy can be emitted over a multiplicity of optical wavelengths, frequencies, and pulse durations to achieve both OCT imaging and heating of the nanoparticles. In one example, the heating of the nanoparticle with light near the green spectrum can be used to cause cellular death in the tissue targeted and localized with nanoparticles. In order to achieve heating nanoparticle and killing of the cell, the pulse duration can be about 10 nanoseconds or less for particles smaller than 100 nm. One of skill in the art will appreciate that different pulse durations can used for different sized nanoparticles in order to achieve heating of the nanoparticle and cellular death. The principle of selective photothermolysis can be used to specify the appropriate pulse duration for targeted particles or clusters of particles of a given size. If mechanical damage is to be achieved, the pulse duration can be selected so that generated acoustic energy is confined in the particle or clusters of particles.

Advantages of Magneto-Motive Ultrasound (MM-US)

Magneto-motive ultrasound (MM-US) provides several advantages over other imaging modalities. Since MRI utilizes static magnetic field, direct application of this imaging approach cannot place magnetic nanoparticles in motion. Further, since MRI is an expensive technology, enhancing the diagnostic value of ultrasound may be cost effective for obtaining improved contrast. Second, macrophages are known to be associated with aggressive cancers of greater malignancy. Ultrasound evaluation of solid tumors is currently limited by a lack of sensitivity and specificity. Magneto-motive detection of magnetic nanoparticle-labeled macrophages associated with tumor cells may enhance the sensitivity and specificity of ultrasound diagnostics. For instance, ultrasound screening for prostate cancer via a rectal probe is currently a limited diagnostic modality. The addition of a magnetic probe to an ultrasound device placed over the prostate gland has the potential to improve the sensitivity and specificity of prostate cancer detection. Third, the strong magnetic susceptibility of superparamagnetic and ferromagnetic nanoparticles combined with an externally applied magnetic field is a combinatorial mechanism in biomedicine and research in targeted drug delivery, molecular imaging, magnetic biosensing, and magnetic separation. Inasmuch as SPIO nanoparticles were approved by the FDA in 1996, and are already utilized in clinical applications, many safety concerns of MM-US method have been addressed previously.

A novel diagnostic ultrasound imaging modality to detect SPIO nanoparticles taken up by tissue-based macrophages in a strong, high intensity magnetic field. The frequency response of the ultrasound Doppler signal from the iron-laden tissue was twice the exciting frequency of the input signal as predicted by magnetic force equations. MM-US provide several advantages for the diagnosis and therapy of various diseases.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. An apparatus for imaging and detection, comprising: a magnet field generator configured to apply a magnetic field to a cell with a plurality of metallic nanoparticles, wherein the magnetic field includes a frequency between about 1 to 10 Hz and is at least about 2 T, wherein the magnetic field displaces the metallic nanoparticles positioned in the cell and displaces the cell, wherein the frequency of displacement of the cell is the same as the frequency of the applied magnetic field; and an ultrasound detection system configured to detect the displacement of the cell with the metallic nanoparticles displaced with the magnetic field.

2. The apparatus of claim 1, wherein the ultrasound detection system is selected from the group consisting of color power Doppler, power Doppler, M-mode and B-scan modes.

3. The apparatus of claim 1, wherein the ultrasound detection system further comprises an aperture and a broadband linear array transducer.

4. The apparatus of claim 1, further comprising an energy source with an energy capable of heating the detected cell through the metallic nanoparticles.

5. The apparatus of claim 1, wherein the magnetic field generator is further configured to apply a first magnetic field strength to the cell and apply a second magnetic field strength to the cell, wherein the second magnetic field strength is different from the first magnetic field strength and interacts with the metallic nanoparticles to cause a change in the cell relative to interaction of the cell with the first magnetic field strength.

6. The apparatus of claim 1, wherein the magnet field generator comprises an iron-ferrite core and a solenoid coil.

7. A method for imaging, comprising the steps of: applying a magnetic field to a cell, wherein the cell comprises a metallic composition and the magnetic field displaces the metallic composition and the cell, wherein the magnetic field includes a frequency between about 1 to 10 Hz and is at least about 2 T, wherein the frequency of the displacement of the cell is twice as the frequency of the applied magnetic field; and detecting the cell by an ultrasound detection system by detecting the displacement of the cell caused by the magnetic field with the metallic composition.

8. The method of claim 7, wherein the step of applying the magnetic field to the cell further comprises using a magnetic field generator to apply the magnetic field.

9. The method of claim 8, wherein the magnetic field generator further comprises a solenoid, a function generator, a current amplifier and a regulated DC power supply.

10. The method of claim 7, wherein the metallic composition is configured to localize in the cell membrane, in the cell cytoplasm, or on the cell surface.

11. The method of claim 7, wherein the step of detecting the cell further comprises using an ultrasound detection system selected from the group consisting of color power Doppler, power Doppler, M-mode and B-scan modes.

12. The method of claim 7, wherein the cell comprises at least a macrophage, a cancer cell, or a component of iron-laden tissue.

13. The method of claim 7, further comprising the step of pulsing the magnetic field.

14. A method for imaging and detecting, comprising the steps of: applying a sinusoidal magnetic field to a cell including a frequency between about 1 to 10 Hz and is at least about 2 T at its sinusoidal peak, wherein the cell comprises a metallic composition and the sinusoidal magnetic field displaces the metallic composition and the cell; and detecting the cell by an ultrasound detection system and detecting the displacement of the cell caused by the sinusoidal magnetic field with the metallic composition.

15. The method of claim 14, wherein the detecting step further comprises detecting an ultrasound signal intensity and displacement proportional to the concentration of the metallic composition.

16. The method of claim 14, wherein detecting the displacement of the cell further comprises detecting the internal strain field of the metallic composition ($\epsilon_{ij}(r, r_o)$) as a tensor quantity given by $$\varepsilon(r, r_0) = \frac{\partial u(r, r_0)}{\partial x_j},$$

where $u_i(r, r_o)$ is the i'th component of the displacement field, $x_j$ is the $j^{th}$ coordinate direction, and $r_o$ is the metallic composition position.

17. The method of claim 14, wherein the step of applying the sinusoidal magnetic field further comprises applying a first magnetic field strength to the cell and applying a second magnetic field strength to the cell, wherein the second magnetic field strength is different from the first magnetic field strength and interacts with the metallic composition to cause a change in the cell relative to interaction of the cell with the first magnetic field strength.

* * * * *